(12) United States Patent
Bunce et al.

(10) Patent No.: US 6,203,498 B1
(45) Date of Patent: Mar. 20, 2001

(54) ULTRASONIC IMAGING DEVICE WITH INTEGRAL DISPLAY

(75) Inventors: Steven Bunce, Sedro Wooly; Lauren S. Pflugrath, Seattle, both of WA (US)

(73) Assignee: Sonosite, Inc., Bothell, WA (US)

(*) Notice: Subject to any disclaimer, the term of this patent is extended or adjusted under 35 U.S.C. 154(b) by 0 days.

(21) Appl. No.: 09/306,372

(22) Filed: May 6, 1999

Related U.S. Application Data

(63) Continuation-in-part of application No. 09/167,964, filed on Oct. 6, 1998, which is a continuation-in-part of application No. 08/826,543, filed on Apr. 3, 1997, now Pat. No. 5,893,363, which is a continuation-in-part of application No. 08/672,782, filed on Jun. 28, 1996, now Pat. No. 5,722,412.

(51) Int. Cl.$^7$ ............................................. A61B 8/00
(52) U.S. Cl. .................................. 600/446; 600/440
(58) Field of Search .................................. 600/437, 440, 600/446, 459, 443, 447; 73/625, 626, 609

(56) References Cited

U.S. PATENT DOCUMENTS

| | | | |
|---|---|---|---|
| 5,640,960 | * 6/1997 | Jones et al. | 600/453 |
| 5,722,412 | 3/1998 | Pflugrath et al. | 128/662.03 |
| 5,763,785 | * 6/1998 | Chiang | 73/609 |
| 5,817,024 | 10/1998 | Ogle et al. | 600/447 |
| 5,893,363 | 4/1999 | Little et al. | 600/447 |
| 5,964,709 | * 10/1999 | Chiang et al. | 600/447 |

* cited by examiner

Primary Examiner—Marvin M. Lateef
Assistant Examiner—Ali M. Imam
(74) Attorney, Agent, or Firm—Townsend and Townsend and Crew LLP

(57) ABSTRACT

A hand held ultrasonic imaging device is provided as an integral unit with all components and circuitry necessary for both image acquisition and image display included in a single enclosure. Usually, the device will also include an on-board battery so that it can be used without any power cords or other cables. Preferably, the device is provided as part of a system including a recharging base unit having a receptacle for removably receiving and storing the hand held device.

21 Claims, 18 Drawing Sheets

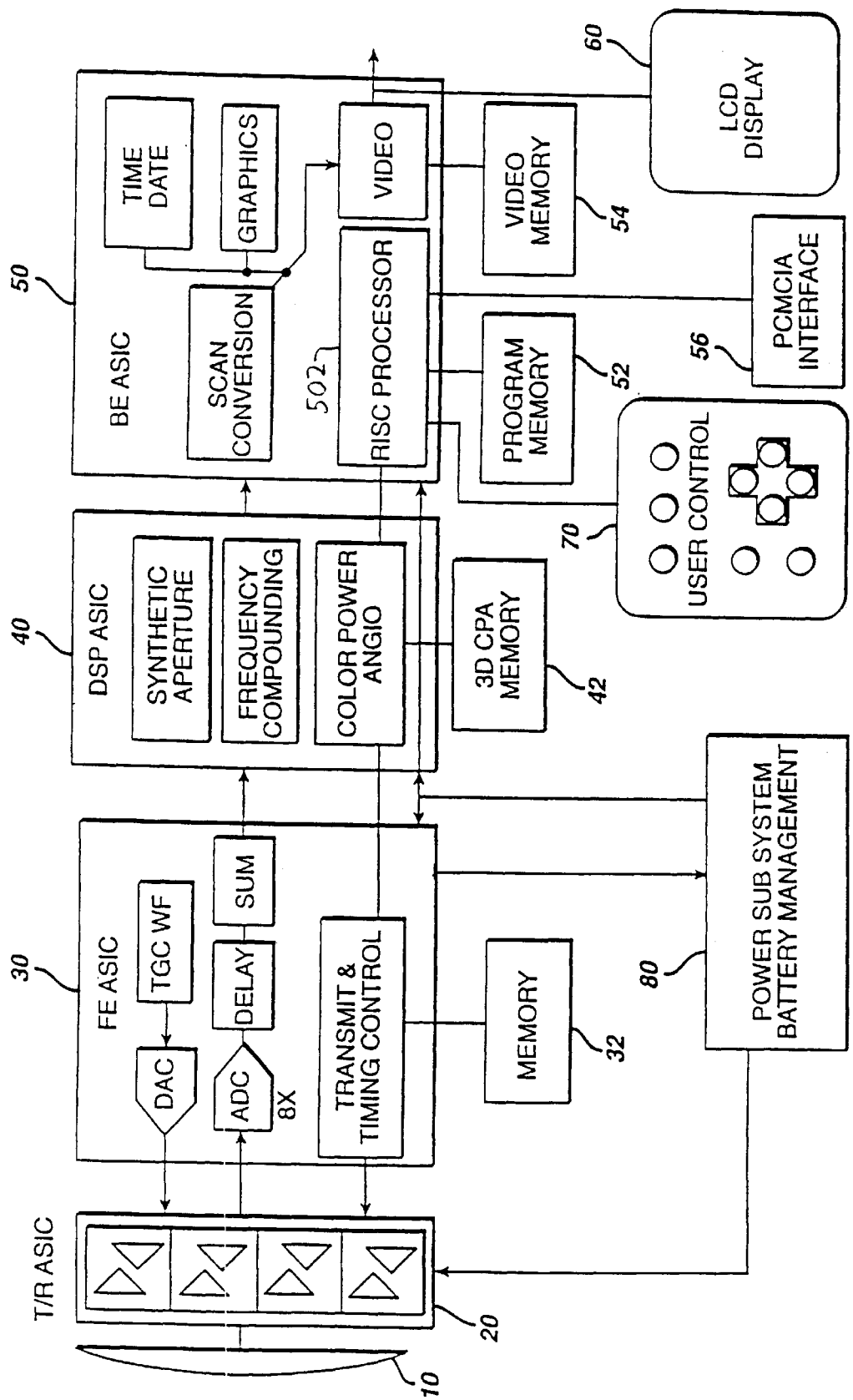

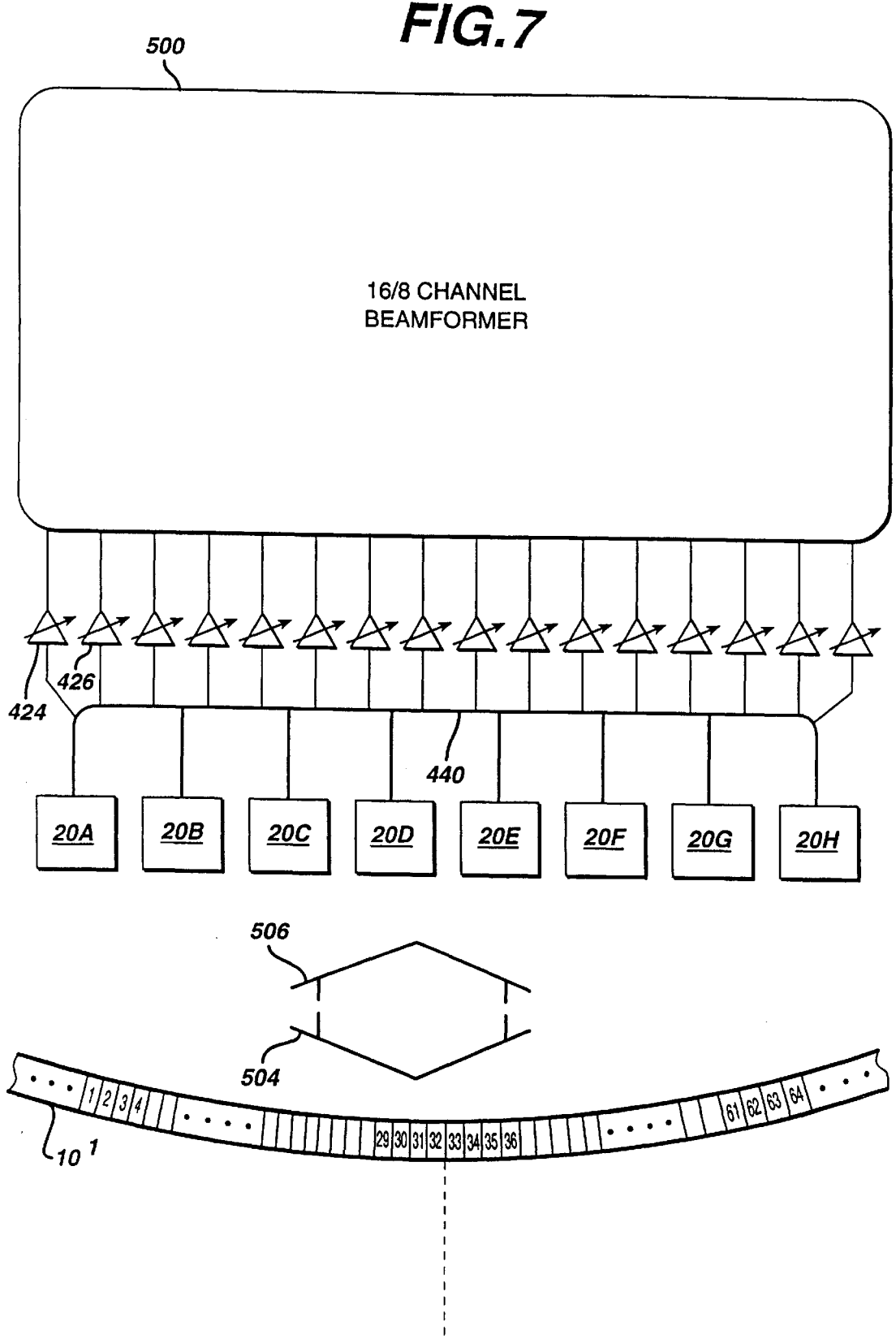

FIG.8

| SWITCH FUNCTION | DESCRIPTION | NUMBER OF CONTACTS |
|---|---|---|
| POWER OFF/ON | SLIDE SWITCH | 1 |
| ACTIVE SCAN/FREEZE | PUSH AND HOLD FOR ACTIVE SCAN | 1 |
| CPA | ENABLES AND DISABLES COLOR POWER ANGIO CPA | 1 |
| DOPPLER/CPA FILTER | HIGH/MEDIUM/LOW BUTTON CYCLES THROUGH 3 SELECTIONS | 1 |
| 3D IMAGING MODE | ENABLES 3D CAPTURE WHEN ENGAGED BEFORE THE ACTIVE SCAN BUTTON IS PUSHED | 1 |
| PRINT | SENDS SERIAL SIGNAL TO PRINTER | 1 |
| CURSOR POSITION | X/Y POSITION OF CURSOR | 4 |
| ENTER | ENTERS SELECTION | 1 |
| MENU | TOGGLES MENU FUNCTIONS OFF AND ON, USES CURSOR AND ENTER. FUNCTIONS: APPLICATION SELECTION USED TO ENTER ALPHA NUMERIC DATA, PATIENT ID, PATIENT NAME, CINE 2D AND 3D REVIEW | 1 |
| MEASURE | ENABLES MEASUREMENTS, USES CURSOR AND ENTER | 1 |
| FOCUS | ENABLES FOCUS MODE, CURSOR UP DOWN POSITIONS FOCUS, CURSOR LEFT RIGHT SELECTS NUMBER OF ZONES | 1 |
| IMAGE | ALLOWS THE USER TO SELECT THROUGH SEVERAL GRAY SCALE CURVES, SPATIAL AND TEMPORAL FILTERS WITH IN A PREDETERMINED SET OF SETUPS FOR A SELECTED APPLICATION | 2 |
| DEPTH | UP/DOWN, 5 DEPTH SELECTIONS | 2 |
| TGC GAIN | UP/DOWN | 2 |
| BRIGHTNESS | LCD DISPLAY CONTROL UP/DOWN | 2 |
| CONTRAST | LCD DISPLAY CONTROL UP/DOWN | 2 |

ULTRASONIC IMAGING DEVICE WITH INTEGRAL DISPLAY

This application is a continuation-in-part of U.S. application Ser. No. 09/167,964, filed on Oct. 6, 1998, which was a continuation-in-part from U.S. application Ser. No. 08/826,543, filed on Apr. 3, 1997, now U.S. Pat. No. 5,893,363, which was a continuation-in-part of U.S. application Ser. No. 08/672,782, filed on Jun. 28, 1996, now U.S. Pat. No. 5,722,412, the full disclosures of which are incorporated herein by reference.

BACKGROUND OF THE INVENTION

1. Field of the Invention

The present invention relates generally to medical devices and methods and, more particularly to a fully integrated hand held ultrasonic diagnostic instrument.

As is well known, modem ultrasonic diagnostic systems are large, complex instruments. Today's premium ultrasound systems, while mounted in carts for portability, continue to weigh several hundred pounds. In the past, ultrasound systems such as the ADR 4000 ultrasound system produced by Advanced Technology Laboratories, Inc. were smaller, desktop units about the size of a personal computer. However, such instruments lacked many of the advanced features of today's premium ultrasound systems such as color Doppler imaging and three dimensional display capabilities. As ultrasound systems have become more sophisticated they have also become bulkier.

However, with the ever increasing density of analog and digital electronics, it is now possible to foresee a time when ultrasound systems will be able to be miniaturized to a size even smaller than their much earlier ancestors. The physician is accustomed to working with a hand held ultrasonic scanhead which is about the size of an electric razor. It would be desirable, consistent with the familiar scanhead, to be able to compact the entire ultrasound system into a scanhead-sized unit. It would be further desirable for such an ultrasound instrument to retain as many of the features of today's sophisticated ultrasound systems as possible, such as speckle reduction, color Doppler and three dimensional imaging capabilities.

Ultrasonic imagining devices incorporating an entire ultrasound system into a scanhead-sized unit will be referred to hereinafter as "fully integrated" devices. In addition to a primary objective of compactness, as set forth above, such fully integrated ultrasound imaging devices would desirably possess a number of other features and characteristics which would benefit the user. For example, it would be desirable for the fully integrated device to operate free from connecting cords, cables, and other attachments, such as power cords. In particular, it would be desirable if such fully integrated devices included an on-board battery which is configured and packaged to permit easy recharging, preferably as part of a storage system where the imaging device is stowed between successive uses. Such storage systems for the device would further preferably provide for protection of the device while maintaining the device in an orientation which permits the viewing of stored images. Of course, the device should also be configured so that the image can be viewed in realtime as the device is scanned across a patient. The device should preferably include a user interface which is both convenient and reconfigurable. Thus, it would be beneficial for the device to have one or more conveniently located dedicated-function keys or buttons as well as having multi-function keys and buttons and/or a full function keyboard to permit more sophisticated and a larger variety of functions. At least some of these objectives will be met by the devices, systems, and methods of the present invention as set forth hereinafter and in the claims.

2. Description of the Background Art

Related patents and pending applications which are commonly assigned with the present application include U.S. Pat. Nos. 5,722,412 and 5,817,024; and U.S. Ser. Nos. 08/826,543 and 09/167,964, the full disclosures of which are incorporated by reference.

SUMMARY OF THE INVENTION

The present invention provides hand held ultrasound devices, systems, and methods for their use. The devices comprise an enclosure having a front, a top, and a bottom. A display, typically a liquid crystal display (LCD), is disposed in an upper section of the front of the enclosure, and an acoustic window is disposed at or near the bottom of the enclosure. An ultrasonic transducer for obtaining an ultrasonic image, typically a transducer array, is located within the enclosure near the acoustic window, and transceiver circuitry (and any other circuitry necessary for forming and controlling the image such as beamformer circuitry when a transducer array is being used) is also located within the enclosure. User controls are located on front of the enclosure below the display and above the acoustic window to permit a user to control and manipulate an image acquired by the transducer through the acoustic window and present it on the display.

In a first specific aspect of the present invention, the device is fully integrated and includes an on-board rechargeable battery. While it is possible to configure the device for powering through an external source, e.g., using a line power cord, the need to plug-in the device is inconvenient. The devices with batteries are preferably incorporated into systems comprising a recharger, preferably in the form of a tabletop base unit having a receptacle for removably receiving the ultrasonic device. Conveniently, mating electrical connectors can be provided on the bottom of the device and within the receptacle so that the hand held device will be connected to the recharging circuitry automatically when the device is placed into the base unit receptacle. By providing such continuous recharging, the imaging device will always be ready for removal and use in scanning a patient. As described in more detail below, the device may be used for realtime image viewing as it scanned across the patient. Additionally, imaging device may be viewed while placed back into the base unit where an acquired image can be displayed and manipulated using the controls on the device. When used with the base unit, the hand held device will preferably further include a handle formed in or on the top of the enclosure. The handle facilitates both removal and replacement into the base unit as well as manipulation of the device during the imaging step.

In a preferred aspect of the device, the display may be attached to the enclosure in a variety of ways. Most simply, the display will be positioned in a fixed orientation relative to the enclosure, usually being inclined in an upward manner to facilitate viewing during use and when in the base unit. In a preferred aspect, the display may be pivotally attached to the enclosure so that its viewing angle may be adjusted. Usually, the display will be moveable between a parallel orientation with the front face of the base unit to an angle of from 30° to 90° relative to the plane of the face.

The nature of the transducer circuitry will depend on the nature of the ultrasonic transducer. In the case of an array transducer, the circuitry will further include a beamformer coupled to the transceiver circuit for controlling transmission of ultrasonic waves by the individual elements of the array transducer and for delaying and combining echo signals received by said elements to form an ultrasonic beam. Usually, the transceiver circuit will include transducer element drivers responsive to said beamformer for selectively exciting said transducer elements. A multiplexor circuit, coupled to said transducer element drivers, said transducer elements, and the beamformer for alternately causing said transducer elements to be excited by said drivers and to receive echo signals for said beamformer will also be provided.

A wide variety of both dedicated and multi-function buttons, keys, switches and the like may be provided as part of the controls on the front of the enclosure. For example, the controls will usually comprise an on and off switch, and will usually further comprise an operating mode selector which permits selection of specific modes, such as B mode, Doppler, and the like. The controls will preferably further include a cursor control which permits the user to select from control options presented on the display. A particularly preferred form of cursor comprises a roller ball which is recessed in the front face of the enclosure. Recess of the roller ball protects the roller ball against both accidental movement and against damage when the unit is dropped. Other controls which may be provided include a dedicated freeze-frame control button, a dedicated replay control button, function selector buttons typically arranged in an array adjacent to the side of the display, and the like. In order to permit maximum flexibility of operation, it will particularly preferred to provide a full function alphanumeric keyboard on the front face of the device.

The present invention further provides methods for ultrasonically imaging a patient. In a first aspect, the methods comprise providing a hand held ultrasonic device in a recharger unit, such as the base unit described above. The hand held ultrasonic device is removed from the recharging unit, typically by pulling on a handle formed in or at the top of the device. After removal from the recharger unit, the hand held device will be powered by a battery within the device which has been charged by the recharger unit. An acoustic window on the hand held ultrasonic device is then scanned over the patient, for example over the abdomen of the patient in performing gynecological examinations. An image resulting from the scanning is viewed on a display on the hand held device itself. In a first instance, the image can be viewed while the device is scanned over the patient so that realtime images can be observed. Alternatively or additionally, the images obtained while scanning may be stored within the device itself and replayed after the scanning is completed. The replayed images will also be viewed on the display on the hand held device itself, and the hand held device may be optionally replaced in the recharger base unit for such subsequent viewing. The stored images may also be downloaded from the hand held device to other viewing and analysis equipment.

In a second aspect of the method, imaging the patient comprises providing a hand held ultrasonic device having an acoustic window, an ultrasonic transducer, and a display all within a common enclosure. The enclosure is manually moved so that the acoustic window scans a target region of the patient, and an image which results from such scanning is viewed on the display in the hand held device itself. Preferably, all power for the imaging will be provided by a battery within the enclosure, and the hand held device will be free from all connections to external equipment and components. Of course, the hand held device may at other times be selectively connected to other equipment, such as a battery charger, computer or other analysis equipment for downloading images, or the like. It is preferred only that the hand held device be free from external connections during the actual image scanning step. As such, it is desirable that the image be produced solely by circuitry and components within the enclosure itself. Optionally, the display on the enclosure may be oriented or adjusted relative to the enclosure itself in order to facilitate viewing during the scanning step. In other instances, however, the display will be fixed relative to the enclosure.

BRIEF DESCRIPTION OF THE DRAWINGS

FIG. 1 illustrates in block diagram form the architecture of a hand held ultrasound system of the present invention;

FIG. 7 illustrates the ASIC of FIG. 8 connected to a transducer array and a beamformer; and FIG. 8 is a chart of the user controls of the ultrasound device of FIG. 1.

DESCRIPTION OF THE SPECIFIC EMBODIMENTS

Figure 2B:
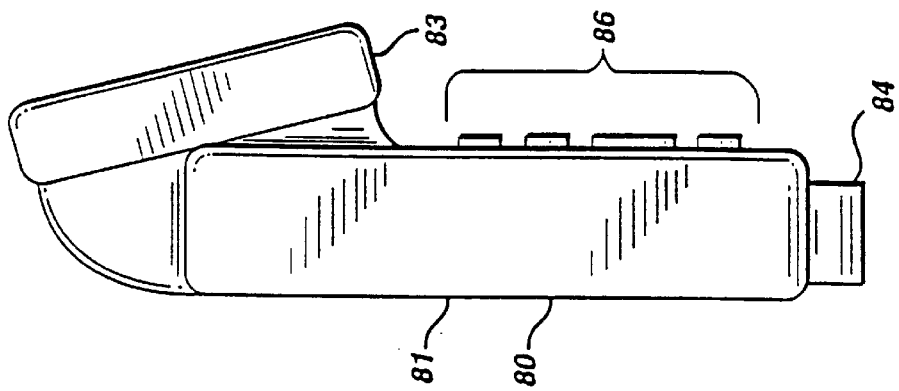
FIGS. 2a and 2b are front and side views of a hand held ultrasound device of the present invention which is packaged as a single unit.

Referring first to FIG. 1, the architecture of a hand held ultrasound system of the present invention is shown. It is possible to package an entire ultrasound system in a single hand held unit only through judicious selection of functions and features and efficient use of integrated circuit and ultrasound technology. A transducer array 10 is used for its solid state, electronic control capabilities, variable aperture, image performance and reliability. Either a flat or curved linear array can be used. In a preferred embodiment the array is a curved array, which affords a broad sector scanning field. While the preferred embodiment provides sufficient delay capability to both steer and focus a flat array such as a phased array, the geometric curvature of the curved array reduces the steering delay requirements on the beamformer. The elements of the array are connected to a transmit/receive ASIC 20 which drives the transducer elements and receives echoes received by the elements. The transmit/receive ASIC 30 also controls the transmit and receive apertures of the array 10 and the gain of the received echo signals. The transmit/receive ASIC is preferably located within inches of the transducer elements, preferably in the same enclosure, and just behind the transducer.

Echoes received by the transmit/receive ASIC 20 are provided to the adjacent front end ASIC 30, which beamforms the echoes from the individual transducer elements into scanline signals. The front end ASIC 30 controls the transmit waveform, timing, aperture and focusing of the ultrasound beam through control signals provided for the transmit/receive ASIC. In the illustrated embodiment the front end ASIC 30 provides timing signals for the other ASICs and time gain control. A power and battery management subsystem 80 monitors and controls the power applied to the transducer array, thereby controlling the acoustic energy which is applied to the patient and minimizing power consumption of the unit. A memory device 32 is connected to the front end ASIC 30, which stores data used by the beamformer.

Beamformed scanline signals are coupled from the front end ASIC 30 to the adjacent digital signal processing ASIC 40. The digital signal processing ASIC 40 filters the scanline signals and in the preferred embodiment also provides several advanced features including synthetic aperture formation, frequency compounding, Doppler processing such as power Doppler (color power angio) processing, and speckle reduction.

The ultrasound B mode and Doppler information is then coupled to the adjacent back end ASIC 50 for scan conversion and the production of video output signals. A memory device 42 is coupled to the back end ASIC 50 to provide storage used in three dimensional power Doppler (3D CPA) imaging. The back end ASIC also adds alphanumeric information to the display such as the time, date, and patient identification. A graphics processor overlays the ultrasound image with information such as depth and focus markers and cursors. Frames of ultrasonic images are stored in a video memory 54 coupled to the back end ASIC 50, enabling them to be recalled and replayed in a live Cineloop® realtime sequence. Video information is available at a video output in several formats, including NTSC and PAL television formats and RGB drive signals for an LCD display 60 or a video monitor.

The back end ASIC 50 also includes the central processor for the ultrasound system, a RISC (reduced instruction set controller) processor 502. The RISC processor is coupled to the front end and digital signal processing ASICs to control and synchronize the processing and control functions throughout the hand held unit. A program memory 52 is coupled to the back end ASIC 50 to store program data which is used by the RISC processor to operate and control the unit. The back end ASIC 50 is also coupled to a data port configured as an infrared transmitter or a PCMCIA interface 56. This interface allows other modules and functions to be attached to or communicate with the hand held ultrasound unit. The interface 56 can connect to a modem or communications link to transmit and receive ultrasound information from remote locations. The interface can accept other data storage devices to add new functionality to the unit, such as an ultrasound information analysis package.

The RISC processor is also coupled to the user controls 70 of the unit to accept user inputs to direct and control the operations of the hand held ultrasound system.

Power for the hand held ultrasound system in a preferred embodiment is provided by are chargeable battery. Battery power is conserved and applied to the components of the unit from a power subsystem 80. The power subsystem 80 includes a DC converter to convert the low battery voltage to a higher voltage which is applied to the transmit/receive ASIC 20 to drive the elements of the transducer array 10.

Figure 2A:
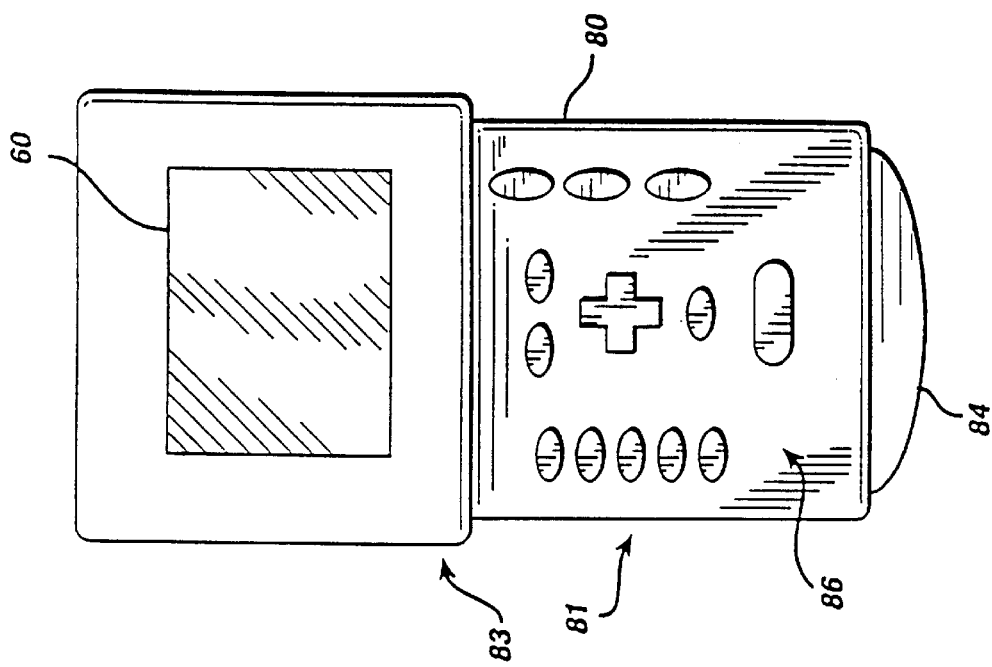

FIGS. 2a and 2b illustrate a one piece unit 80 for housing the ultrasound system of FIG. 1. The front of the unit is shown in FIG. 2a, including an upper section 83 which includes the LCD display 60. The lower section 81 includes the user controls as indicated at 86. The user controls enable the user to turn the unit on and off, select operating characteristics such as the mode (B mode or Doppler), color Doppler sector or frame rate, and special functions such as three dimensional display. The user controls also enable entry of time, date, and patient data. A four way control, shown as a cross, operates as a joystick to maneuver cursors on the screen or select functions from a user menu. Alternatively a mouse ball or track pad can be used to provide cursor and other controls in multiple directions. Several buttons and switches of the controls are dedicated for specific functions such as freezing an image and storing and replaying an image sequence from the Cineloop® memory.

At the bottom of the unit 80 is the aperture 84 of the curved transducer array 10. In use, the transducer aperture is held against the patient to scan the patient and the ultrasound image is displayed on the LCD display 60.

FIG. 2b is a side view of the unit 80, showing the depth of the unit. The unit is approximately 20.3 cm high, 11.4 cm wide, and 4.5 cm deep. This unit contains all of the elements of a fully operational ultrasound system with a curved array transducer probe, in a single package weighing less than five pounds. A major portion of this weight is attributable to the battery housed inside the unit.

Figure 3:
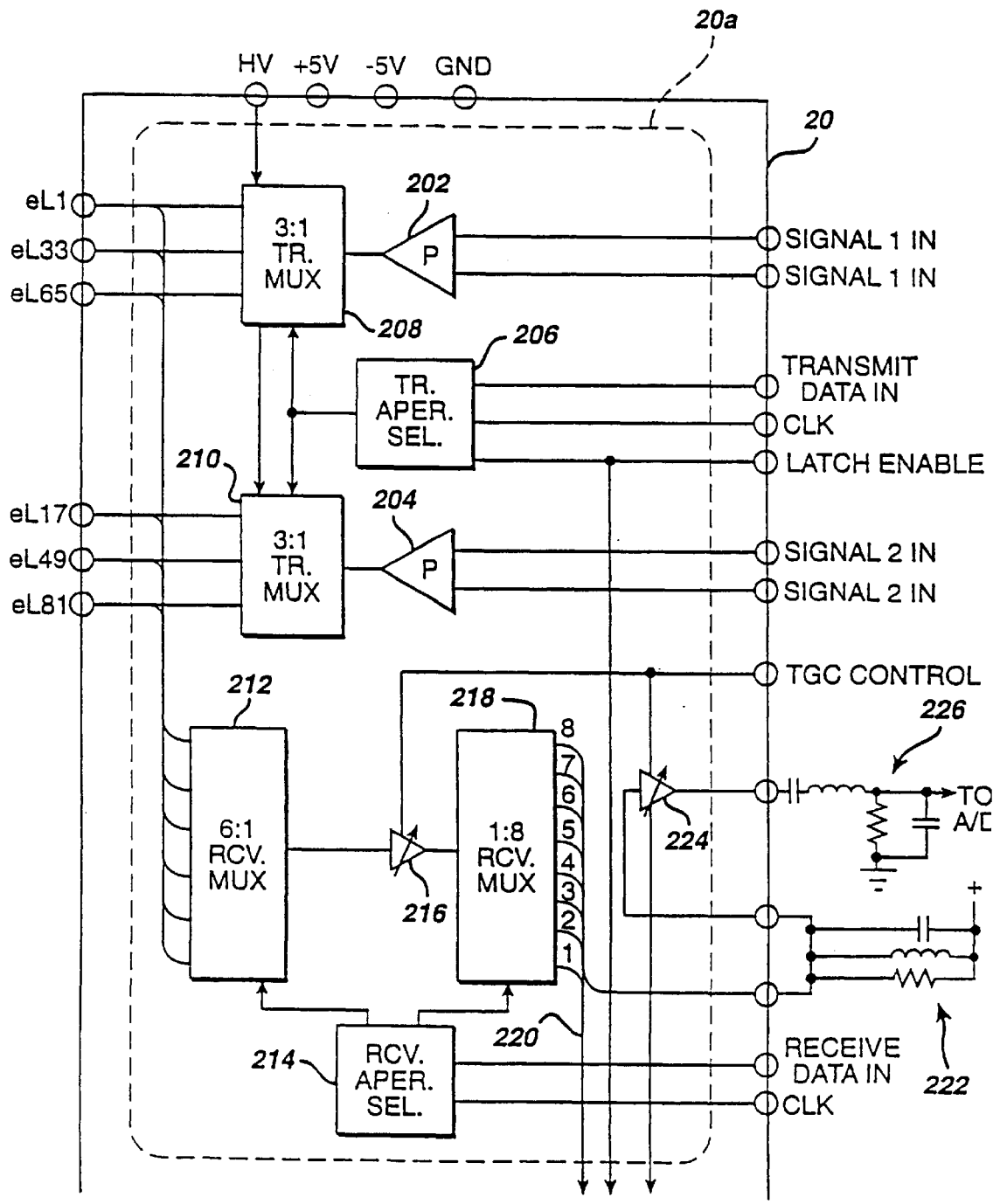
FIG. 3 is a schematic diagram of the transmit/receive ASIC of the ultrasound device of FIG. 1.

Referring now to FIG. 3, the transmit/receive ASIC 20 is shown in greater detail. This ASIC is comprised of sixteen sections, each of which is coupled to six transducer elements of the array 10. The illustrated section 20a is coupled to elements 1, 17, 33, 49, 65 and 81 at the terminals on the left side of the drawing. With six elements per section, the entire ASIC can operate with a 96 element transducer. Each section could be configured to operate with eight elements, in which case the ASIC could control a 128 element transducer, for instance. Prior to the transmission of an ultrasonic pulse for a scanline, a serial stream of data from the front end ASIC 30 is clocked into transmit aperture select logic 206 at the Transmit Data In terminal at the right side of the drawing. The transmit aperture select logic 206 uses this data to set multiplexer switches in 3:1 transmit muxes 208 and 210 for the transducer elements that will be active for the particular scanline. For instance, the next scanline to be transmitted may have a transmit aperture comprising elements 1–32. This requires that transmit mux 208 closes a switch to connect pulser 202 to the element 1 terminal, and the transmit mux 210 closes a switch to connect pulser 204 to the element 17 terminal. In a similar manner the transmit muxes in the other fifteen sections of the ASIC will connect pulsers to element terminals 2–16 and 18–32.

At the times when the connected elements 1 and 17 are to be activated, drive signals for the pulsers 202 and 204 are applied to the Signal 1 In and Signal 2 In terminals by the front end ASIC. For unipolar pulsers the drive signals are applied to single input terminals of each pulser. Alternatively, complementary waveforms are applied at the appropriate times to the paired terminals when bipolar drive signals are used, as illustrated by the paired input terminals for each pulser in this drawing. These drive signals are applied as logic level signals to the pulser inputs, then converted to high voltage driving waveforms by the application of high voltage HV applied to the muxes 208 and 210. It is also possible to fabricate the pulser and mux functions as a single unit, whereby each switch of the muxes is effectively a high voltage pulser. Stated another way, this means that each mux would comprise three separately controlled pursers. Alternatively, the two pulsers at the inputs of the transmit muxes could be deleted and replaced by six pulsers at the outputs of the transmit muxes, however, the illustrated embodiment advantageously requires only two, low voltage pulsers. Continuing with the example of the aperture of elements 1–32, if element 1 is at the periphery of the aperture and element 17 is more central to the aperture, element 1 would be pulsed earlier in time than element 17 to produce a focused transmitted ultrasonic waveform.

Prior to transmission of the scanline a stream of digital data from the front end ASIC is clocked into receive aperture select logic 214 from the Receive Data In terminal connected to receive aperture select logic 214. The receive aperture select logic closes switches in a 6:1 receive mux 212 and a 1:8 receive mux 218 for the proper receive aperture. Like the transmit aperture select logic, the receive aperture select logic includes buffer storage so that data for the next scanline can be received while the ASIC is receiving echoes from the current scanline. The illustrated embodiment is designed for a sixteen element folded receive aperture as shown by the eight data bus lines at the output of the 1:8 receive mux 218. The inputs to the 6:1 receive mux 212 are connected to the six element terminals for section 20*a* and are protected from the high drive voltages by the integration of transmit/receive networks at the mux inputs. The receive aperture select logic 214 connects one of the inputs of the mux 212 to the mux output, and the received signal from the selected element is applied to a first time gain control (TGC) amplifier 216. The gain of this TGC amplifier is controlled by a control signal applied to a TGC Control terminal of the ASIC. The amplification provided by amplifier 216 increases as ultrasonic echoes are received from increasing depths, in the conventional manner. The amplified echo signals are then coupled by the switching of the 1:8 receive mux 218 to one of the data bus lines 220.

Each of the data bus lines 220 is coupled to the same corresponding output of every 1:8 receive mux on the ASIC. The outputs of the mux 218 are numbered from 1–8. Output 1 of each 1:8 receive mux is coupled to the same one of the data lines; output 2 of each 1:8 receive mux is coupled to another one of the data lines; and so forth. The preferred embodiment system uses a sixteen element folded aperture of scanlines transmitted orthogonal to the transducer. This means that two elements of the aperture will have the same receive phases of operation; the sixteen elements of the receive aperture will be paired to have eight receive phases. For instance, if the received scanline is located at the center of an aperture of elements 1–16, elements 1 and 16 will have the same receive timing. Echoes received by element 1 will be connected through mux 212, amplified by TGC amplifier 216, connected through mux 218 and produced as a current output at output 8 of the mux 218. At the same time, an echo received by element 16 will be connected through the muxes of another section of the ASIC, identically amplified by another TGC amplifier, and produced as a current output at output 8 of another 1:8 receive mux. These two currents are identically phased by virtue of the folded aperture, and combine on the data line which is coupled to output 8 of the receive muxes.

The currents on each data line are filtered and converted to voltages by a filter network such as that shown at 222. In the preferred embodiment filter network 222 is external to and coupled to a terminal of the ASIC so that its components and hence its filter characteristic can be easily selected and changed. The filter characteristic is a bandpass chosen to match the passband of the transducer. For a 3.5 MHz transducer the passband could extend from 1.5 to 5.5 MHz, for example. The filter is connected to a current source through the filter impedance to convert the current signals to a single voltage. This voltage reenters the ASIC through another (or the same) ASIC terminal and is applied to the input of a second TGC amplifier 224. The use of two TGC amplifiers enables operation over the wide dynamic range of the two cascaded amplifiers. In the illustrated embodiment a single TGC Control applies the same control characteristic to both TGC amplifiers 216 and 224, but it is also possible to apply separate and different TGC characteristics to the two amplifiers. The amplified echo signals are brought to a final output terminal of the ASIC where they are filtered by a bandpass filter 226 and coupled to an analog to digital (A/D) converter at the input of the beamformer on the front end ASIC.

The separate sections of the transmit/receive ASIC 20 may be contained in separate ASICs or combined so that several sections are integrated on the same ASIC. Preferably all sixteen sections are integrated onto a single ASIC chip.

Thus it is seen that, in the preferred embodiment, the transmit/receive ASIC 20 operates with a 96 element transducer array, and uses a 32 element transmit aperture and a 16 element folded receive aperture. With the use of a synthetic aperture as discussed below, the system exhibits a 32 element aperture on both transmit and receive.

Figure 4:
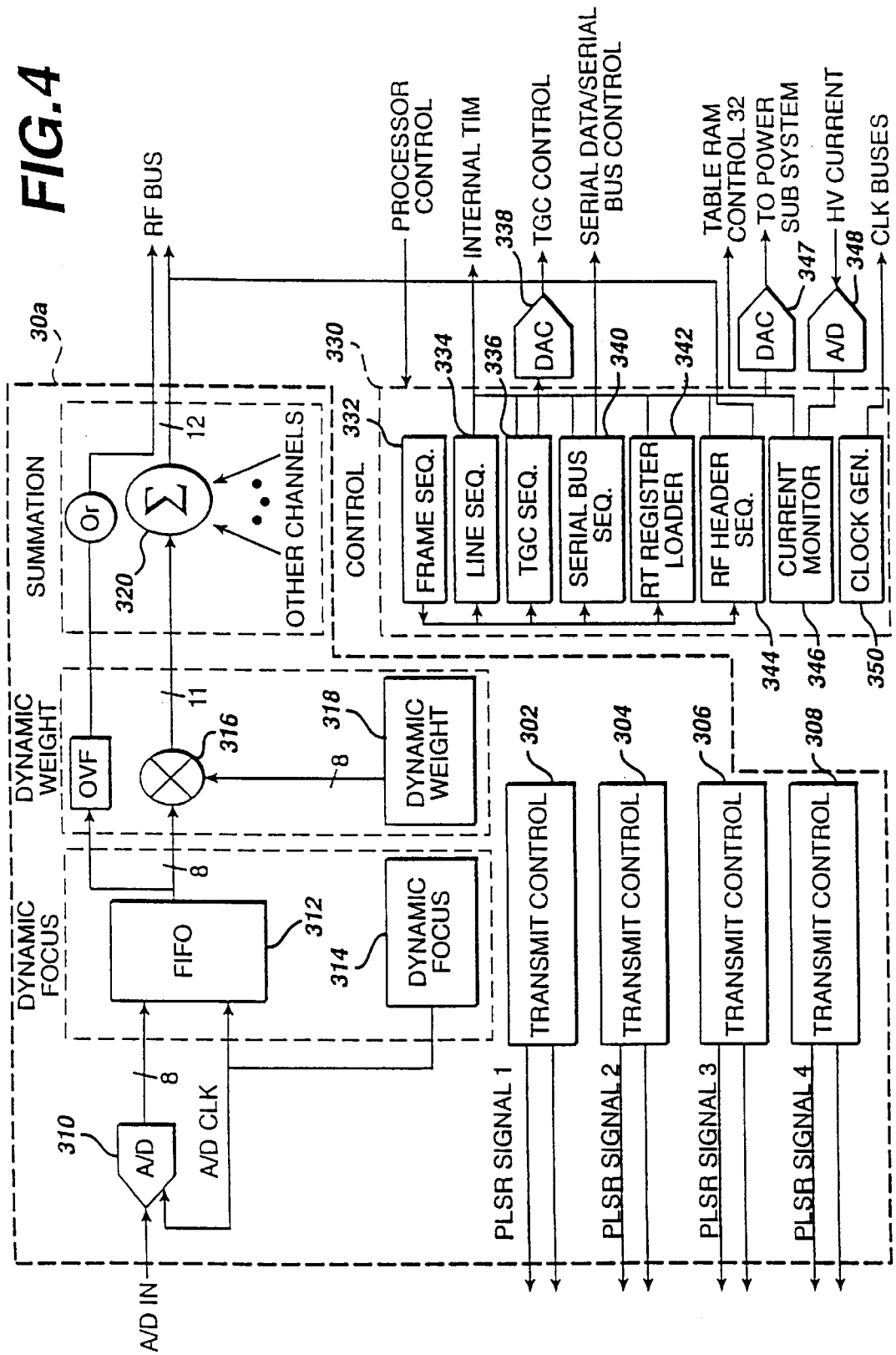
FIG. 4 is a block diagram of the front end ASIC of the ultrasound system of FIG. 1.

Details of the front end ASIC 30 are shown in FIG. 4. This drawing shows one section 30*a* of the front end ASIC 30. There are eight such sections on the front end ASIC to provide beamforming of the eight outputs from the transmit/receive ASIC 20. Each echo signal output is coupled to the input of an A/D converter 310, where the echo signals are converted to digital data. The digital data from each element (or each pair of elements in a folded aperture) is shifted into a first in, first out (FIFO) register 312 by a clock signal A/D CLX. The A/D CLX signal is provided by a dynamic focus timing circuit 314 which defers the start of the clock signal to provide an initial delay, then controls the signal sampling times to provide dynamic focusing of the received echo signals. The length of the FIFO register 312 is determined by the initial delay, the transducer center frequency, the aperture size, the curvature of the array, and the beam steering requirement. A higher center frequency and a curved array will reduce the steering delay requirement and hence the length of the FIFO register, for instance. The delayed echo signals from the FIFO register 312 are coupled to a multiplier 316 where the echo signals are weighted by dynamic weight values stored in a dynamic weight register 318. The dynamic weight values weight the echo signals in consideration of the effects of a dynamic receive aperture such as the number of active elements, the position of an element in the aperture, and the desired apodization function, as the aperture expands by the inclusion of additional outer elements as echoes are received from increasing depths along the scanline. The delayed and weighted echo signals are then summed with appropriately delayed and weighted echo signals from other elements and echo signals from any other delay stages which are coupled in cascade by a summing circuit 320. The beamformed echo signals, together with synchronous overflow bits, are produced as output scanline data on an RF data bus. Accompanying each sequence of scanline echo signals is identifying information provided by an RF header sequencer on the ASIC, which identifies the type of scanline data being produced. The RF header can identify the scanline as B mode echo data or Doppler data, for instance.

Other digital storage devices can be used to provide the beamformer delays, if desired. A dual ported random access memory can be used to store the received digital echo samples, which are then read out from the memory at times or sequences which provide the desired delay for the signals from the transducer elements.

Each section 30a of the front end ASIC includes transmit control circuits 302–308 for four transducer elements of the array. The eight sections thus provide transmit control for 32 elements of the array at the same time, thereby determining the maximum transmit aperture. The transmit control circuits produce pulse waveforms at the desired transmission frequency and at the appropriate times to produce a transmitted acoustic signal which is focused at the desired depth of focus.

The front end ASIC includes a common control section 330 which provides overall realtime control for the transmission and receive functions. The control section 330 is controlled by and receives data under control of the RISC processor located on the back end ASIC. The data tables for a particular imaging mode are loaded into random access memory (RAM) 32 prior to scanning and are loaded into the control section 330 under command of the RISC processor. The control of scanning of individual lines is then controlled and varied in real time. The control section 330 includes a number of sequencers for the sequence of transmit and receive functions. The frame sequencer 332 produces information used by other sequencers which identifies the type of image frame which is to be produced. The frame sequencer may, for example, be loaded with data that defines the next frame as B mode scanlines interspersed between groups of four Doppler scanlines, and that the sequence of scanlines will be all odd numbered scanlines followed by all even numbered scanlines. This information is supplied to the line sequencer 334, which controls the scanlines which are transmitted and received in the proper sequence. In preparation for a new scanline the line sequencer controls the TGC sequencer 336 50 that it will produce the desired sequence of TGC control data. The TGC control data from the TGC sequencer is converted to a voltage signal by a digital to analog converter (DAC) 338 and applied to the TGC Control input terminal(s) of the transmit/receive ASIC 20. The line sequencer 334 also controls the serial bus sequencer 340, which produces serial data on a serial bus for the transmit and receive aperture select logic circuits 206 and 214 on the transmit/receive ASIC. The receive/transmit (RT) register loader 342 controls the loading of data for a new scanline into various registers on both ASICs, including the aperture select logic circuits 206 and 214, the transmit control circuits 302–308, the dynamic focus timing circuit 314 and the dynamic weight register 318. All registers which perform real time functions are double buffered. As discussed above, the various registers are buffered so that the control data can be put on the serial bus and loaded into the various registers during the line preceding the scanline for which the control data is used.

The front end ASIC 30 includes a current monitor circuit 346, which samples the current on the HY bus by way of an A/D converter 348. The current monitor assures patient safety by reducing or completely shutting down the high voltage supply if excessive current levels are detected, thereby protecting the patient from an overheated transducer or unacceptably high acoustic output levels. The current monitor circuit may also be located in the power and battery management sub system 80.

The front end ASIC includes in its control section a clock generator 350 which produces a plurality of synchronous clock signals from which all operations of the system are synchronized. To prevent interference and crosstalk among the closely spaced devices of the system, the video output signal frequency is synchronized to a clock signal of the clock generator, so harmonics of one frequency will not produce interfering components in the other. A crystal oscillator (not shown) is coupled to the front end ASIC 30 to provide a basic high frequency such as 60 MHz from which all of the clock signals of the system may be derived.

Figure 5:
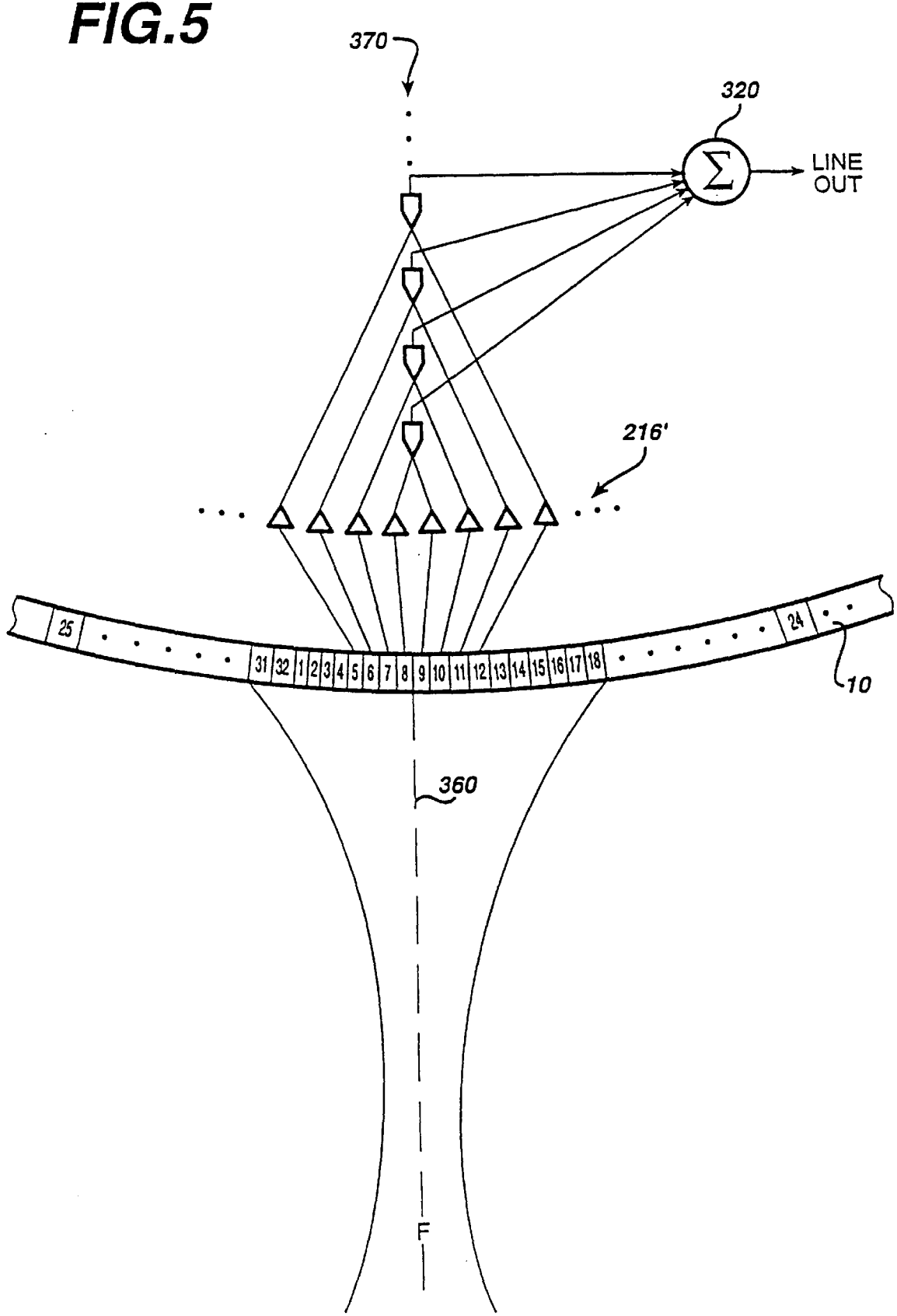
FIG. 5 illustrates the aperture control afforded by the transmit/receive and front end ASICs.

The operation of the transmit/receive and front end ASICs 20 and 30 to produce a synthetic folded aperture scanline from 32 elements of a curved array is illustrated with reference to FIG. 5. In this drawing the ASICs are controlling an aperture of the transducer comprising 32 elements numbered from 25 through 32, then 1 through 24 of the curved array 10. Gathering the full aperture of scanline information requires two transmit sequences of all 32 elements. To transmit, the line sequencer 334, the serial bus sequencer 340, and the RT register loader 342 load the proper transmit mux data into the sixteen transmit aperture select logic circuits 206 and the 32 transmit controllers on the front end ASIC. The aperture select logic then control the 32 transmit muxes to connect pulsers to elements numbered 25–32 and 1–24, the desired transmit aperture. The pulsers are pulsed by the transmit control circuits so as to produce an acoustic wave which is focused at point F in FIG. 5.

Following the first pulse transmission, echoes are received by the center group of elements numbered 1–16, which at that time are connected by the sixteen 6:1 receive muxes and 1:8 receive muxes to eight output data lines. The sixteen receive signals are shown as separate when they pass through the initial TGC amplifiers, eight of which are shown in a row as indicated at 216' in FIG. 5. The like phased signals are then seen to combine in pairs by virtue of the folded aperture where pairs of lines come together at the input of the beamformer delay lines, four of which are shown as indicated at 370. In the illustrated example the scanline 360 extends from the center of the array aperture between elements 8 and 9. This means that echo signals received by elements 8 and 9 will be in phase, and can be combined. Likewise, echoes received by paired elements 7 and 10, paired elements 6 and 11, and paired elements 5 and 12 can also be combined. Thus, following the first transmitted pulse, echoes received by elements 1–16 are delayed by the eight delay FIFOs and summed by the summing circuit 320. This half aperture is then stored for receipt of the other half aperture.

Another acoustic pulse is transmitted by all 32 elements of the aperture. After this second pulse, the receive muxes now connect echoes from elements 25–32 and 17–24 to the beamformer. By virtue of the folded aperture symmetry the echoes from element 32 are paired with echoes from element 17 and the two are combined. Likewise, echoes from element 31 are paired with echoes from element 18, and so forth, out to the most lateral paired elements 25 and 24.

The sixteen received echoes, paired to eight signals by the folded aperture, are appropriately delayed by the eight delay FIFOs and summed to form a second half aperture of the scanline. The two halves of the aperture are now summed as a function of the location of the echo components along the scanline of the two sequences. Thus, the complete aperture has been formed by combining the separate receptions of echoes from the inner sixteen elements of the aperture, then from the outer sixteen elements. A precisely beamformed synthetic aperture signal is produced by maintaining identical conditions of TGC control during both reception intervals. The dynamic weighting and dynamic focusing affect the two reception sequences differently by reason of the differing aperture locations of the receiving elements during the two sequences. The delays applied by the FIFOs during the two sequences will be different by reason of the differing locations across the aperture of the receiving elements from one sequence to the next.

Figure 6:
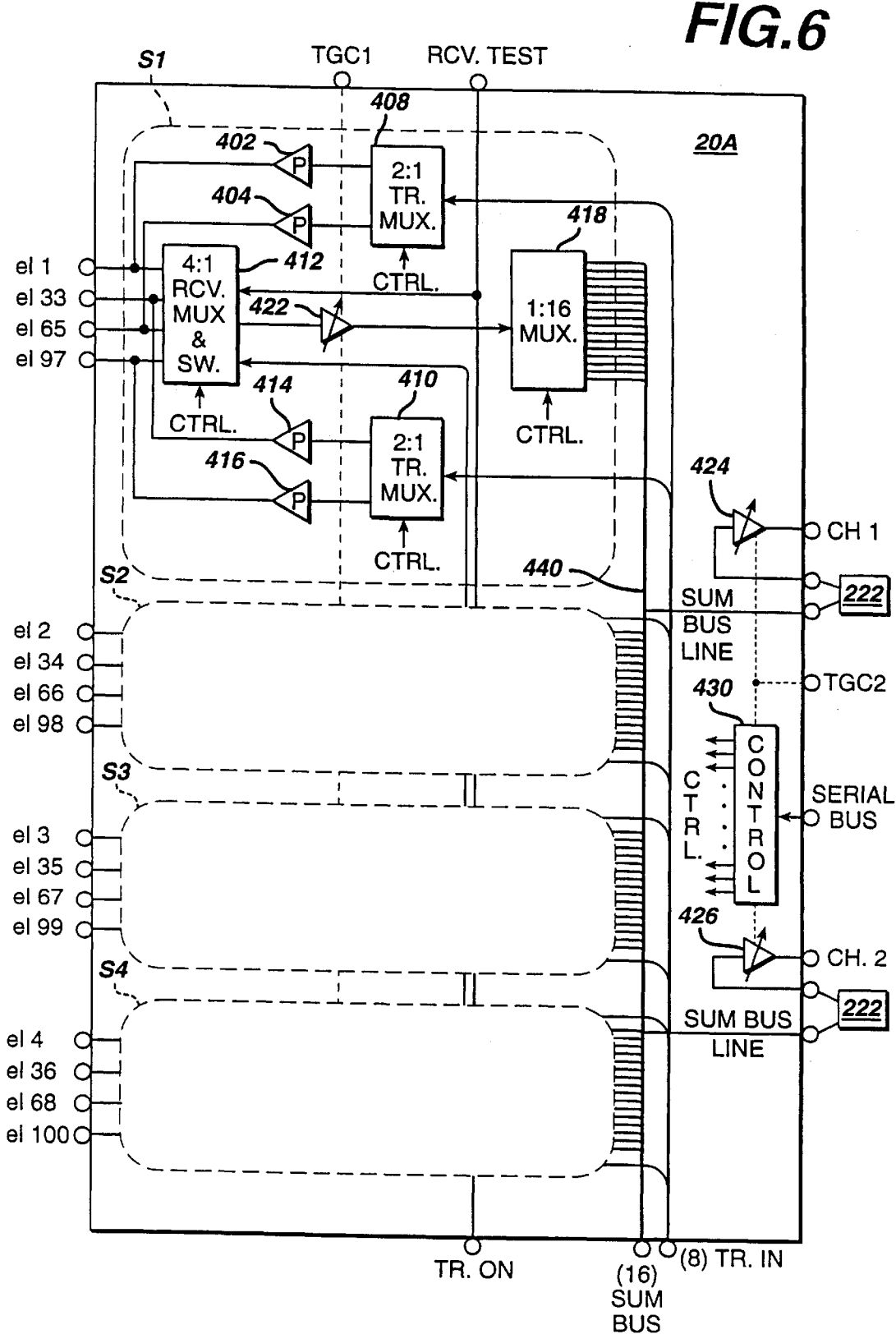
FIG. 6 illustrates in block diagram form a second embodiment of the present invention.

A preferred transmit/receive ASIC 20A is shown in FIG. 6. The signal paths of the ASIC 20A are divided into four identical sections S1, S2, S3, and S4. In this drawing section S1 is shown in internal detail. The section S1 includes two 2:1 transmit multiplexers 408 and 410, each of which is responsive to a pulser signal on one of eight (8) Transmit In lines. Each 2:1 Transmit Multiplexer has two outputs which drive pulsers 402, 404, and 414, 416, the outputs of which are coupled to ASIC pins to which transducer elements are connected. In the illustrated embodiment the 2:1 Transmit Multiplexer 408 is coupled to drive either element 1 or element 65, and the 2:1 Transmit Multiplexer 410 is coupled to drive either element 33 or element 97. The 2:1 Transmit Multiplexers of the other sections of the ASIC are each similarly coupled to four transducer elements. With a separate pulser for each transducer element, the ASIC 20A can independently and simultaneously drive eight of the sixteen transducer elements to which it is connected.

The transducer element pins to which the pulsers of each section are coupled are also coupled to the inputs of a 4:1 Receive Multiplexer and Switch 412. When the pulsers are driving the transducer elements during ultrasound transmission, a signal on a Transmit On line which is coupled to all of the 4:1 Receive Multiplexers and Switches on the ASIC switches them all into a state which presents a high impedance to the high voltage drive pulses, thereby insulating the rest of the receive signal paths from these high voltage pulses. All of the 4:1 Receive Multiplexers and Switches of the ASIC are also coupled to a Receive Test pin of the I.C., by which a test signal can be injected into the receive signal paths and propagate through the receiver system. During echo reception each 4:1 Receive Multiplexer and Switch couples the signals of one of the four transducer elements to which it is coupled to a 1:16 Multiplexer 418 by way of a first TGC stage 416. The gain of the first TGC stages on the ASIC is controlled by a voltage applied to a TGC1 pin of the ASIC which in a constructed embodiment, comprises two pins for application of a differential control voltage. The 1:16 Multiplexers of each section of the ASIC each route received echo signals to one of the sixteen (16) lines of a Sum Bus 440. Two of the sixteen Sum Bus lines are shown at the right side of the drawing, and are coupled to filter circuits 222. The filtered bus signals are coupled to input pins leading to two second TGC stages 424 and 426, the gain of which is controlled by the voltage applied to one or two TGC2 pins. The outputs of these second TGC stages in the illustrated embodiment are connected to output pins leading to channels 1 and 2 of the ultrasound system's beamformer.

The ASIC 20A also includes a control register 430 which receives control signals over a serial bus from the beamformer. The control register distributes control signals to all of the multiplexers of the ASIC as shown by the Ctrl. input arrows.

A constructed embodiment of ASIC 20A will have a number of pins for supply and bias voltages and ground connections and are not shown in the drawing. A system using the ASICs of the present invention exhibits an N:1, 1:M architecture, where N is the number of transducer elements divided by the maximum aperture size, and M is the number of beamformer channels. These ASICs can be used to connect a wide variety of transducer arrays of various numbers of elements to beamformers of different numbers of channels in numerous ways. An example of this versatility is shown in the system of FIG. 7, which shows a transducer 10' coupled (as indicated by arrows 506, 504) to eight ASICs 20A–20H, the Sum Bus 440 of which is coupled by the sixteen second TGC stages of the ASICs to a sixteen channel beamformer 500. (For clarity of illustration the second TOC stages are separately illustrated, although they are in fact integrated on the ASICs.) In this example the eight ASICs, each having sixteen pins for connection to transducer elements, are connected to separately drive all 128 elements of transducer array 10'. The 2:1 Transmit Multiplexers of the eight ASICs are capable of driving 64 elements at once, and thus can operate the transducer array to have a 64 element transmit aperture, represented by transducer element 1–4 . . . 29–36 . . . 61–64 in the drawing. This 64 element aperture is centered between elements 32 and 33. This arrangement is capable of driving all of the elements of a 64 element aperture for each transmitted ultrasound wave. The control registers of the eight ASICs 20A20H can be conveniently coupled to separate lines of an eight line data bus from the beamformer, each line serving as a serial bus for a particular control register, thereby enabling all eight control registers to be loaded simultaneously.

Echo signal reception over the full 64 element aperture can be accomplished in several ways. One is to employ a folded and synthetic aperture as described in FIG. 5. After a first wave transmission the echoes on elements 17–32 are received and folded together with the echoes from elements 48–33. That is, one Sum Bus line would have the echoes from elements 17 and 48 multiplexed onto it, another Sum Bus line would have the echoes from elements 18 and 47 multiplexed onto it, and so forth. These sixteen folded signals are appropriately delayed and combined to develop a focused signals. After a second wave transmission the outer elements of the aperture are used for folded reception, delayed and combined with each other and the first focused signals to complete the aperture.

This N:1, 1:M ASIC architecture can be used with an eight channel beamformer 500 in place of the 16 channel beamformer by use of the folded and synthetic aperture techniques, or by use of a coarse aperture reception technique, as described in U.S. Pat. No. 4,542,653. In this technique, adjacent elements which were independently excited during beam transmission are paired during reception by combining their received signals and using the same focusing delay for them. Effectively, this means that the transducer pitch is coarser during reception by a factor of two. While this will raise the level of the grating lobes of the received beam pattern, the combined transmit and receive beam patterns will still be acceptable, and the system will benefit by the higher sensitivity of a larger receive aperture. If the grating lobes should prove objectionable, they can be reduced by using an aperiodic aperture, in which the number of elements combined as groups vary from group to group across the aperture. The aperiodic aperture will effectively blend the grating lobe effects into a uniform image background.

In one such arrangement the signals received by four transducer elements are directed to the same Sum Bus line, by suitably programming the 1:16 Multiplexers, for application to the inputs of each of eight beamformer channels. This allows the received signals from elements 17 and 18 to be combined with the received signals from elements 47 and 48 on the same Sum Bus line, and all four signals coupled to the input of one beamformer channel. Thus, both coarse receive and folded aperture techniques are employed simultaneously. A thirty-two element aperture can be received following a single transmitted wave, or a sixty-four element aperture formed by the synthetic aperture technique with two wave transmissions. If only a fine receive aperture is used, the receive aperture is restricted to thirty-two elements with use of the folded and synthetic aperture techniques, or sixteen elements with the folded or synthetic aperture techniques alone.

The front end ASIC of FIG. 4 is seen to have four transmit control circuits for each receive channel, a total of 32 transmit control circuits in all. These 32 transmit control circuits can be coupled to the sixty-four pulser inputs of the eight transmit/receive ASICS of FIG. 7 by coupling one transmit control circuit to both inputs of each pair of Transmit Multiplexers 408, 410 and programming one of the Transmit Multiplexers to be enabled and the other disabled through the control signals of the control register 430. This effectively converts each pair of 2:1 Transmit Multiplexers to operation as a 4:1 Transmit Multiplexer, giving a maximum transmit aperture of thirty-two independently controlled elements.

The foregoing examples apply to a received beam that is directed orthogonal to the center of the aperture of the array. If the received beam is to be steered off the orthogonal line as well as focused, the folded aperture technique cannot be used, since varying delays have to be employed across the full active aperture.

Variations of the ASIC 20A will also be apparent to those skilled in the art. If all of the transducer elements are to be driven simultaneously and independently, the 2:1 Transmit Multiplexers can be eliminated and the pulsers 402, 404, 414, 416 driven directly. The 1:16 Multiplexers could be expanded to 1:32 for a thirty-two channel beamformer, which could control 64 element apertures through the folded and coarse aperture techniques with no degradation in the frame rate. The 4:1 Receive Multiplexers and Switches could be partitioned into two 2:1 Receive Multiplexers and Switches, each coupled to its own bus multiplexer. Such variations will accommodate different apertures for operation at different and higher image frame rates.

The back end ASIC 50 is the location of the RISC processor 502, which is used to coordinate the timing of all of the operations of the hand held ultrasound system. The RISC processor is connected to all other major functional areas of the ASICs to coordinate processing timing and to load buffers and registers with the data necessary to perform the type of processing and display desired by the user. Program data for operation of the RISC processor is stored in a program memory 52 which is accessed by the RISC processor. Timing for the RISC processor is provided by clock signals from the clock generator on the front end ASIC 30. The RISC processor also communicates through an infrared beam interface, by which the processor can access additional program data or transmit image information remotely. The infrared interface can connect to a telemetry link for the transmission of ultrasound images from the hand held unit to a remote location, for instance. A PCMCIA data interface may also or alternately be employed for data communication, as desired.

The RISC processor is operated under user control by commands and entries made by the user on the user control 70. A chart showing control functions, the type of controls, and their description is shown in FIG. 8. It will be appreciated that a number of functions, such as patient data entry, Cineloop® operation, and 3D review, will operate through menu control to minimize the number of key or button controls on the small hand held unit. To further simplify the unit a number of operating functions are preprogrammed to specific diagnostic applications and will operate automatically when a specific application is selected. Selection of B mode imaging will automatically invoke frequency compounding and depth dependent filtering, for instance, while a four multiplier filter will automatically be set up as a wall filter when Doppler operation is selected. The menu selection of specific clinical applications can automatically invoke specific feature settings such as TGC control characteristics and focal zones, for example.

Figure 9:
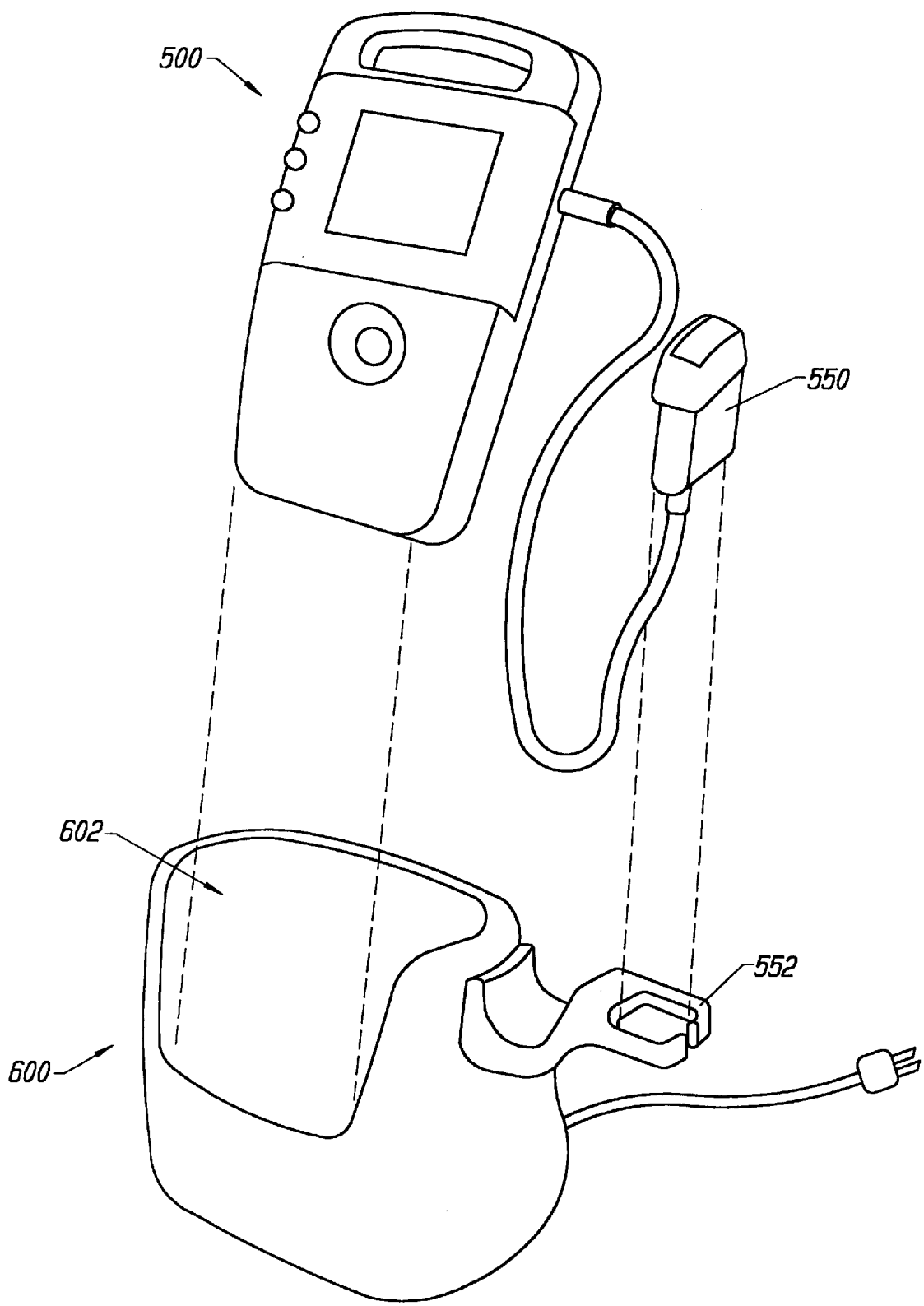
FIG. 9 is a perspective view of an ultrasonic imaging system comprising a hand held ultrasonic device in combination with a recharger in the form of a base unit which removably receives the device.

The hand held ultrasonic imaging devices of the present invention will preferably be incorporated in systems which also include a recharger for the battery within the device. The recharger will typically be in the form of a table-mounted base unit which includes a receptacle or slot for removably receiving the hand held device. The recharging base unit will provide for continuous recharging of the battery when the device is not in use and further provide for protection and storage of the device. Optionally, the recharging base unit may include features which permit or facilitate viewing of the display on the device, data transferred between the hand held device and external devices, reprogramming of the device, and other capabilities. As is illustrated in FIG. 9, a hand held ultrasonic imaging device 500 (described in more detail below) is removably received in receptacle 602 of a recharging base unit 600. Optionally, the hand held ultrasonic imaging device may include a plug-in (auxilliary) scanning head 550 which permits scanning when the device is held in the base unit 600. The base unit may include a bracket 552 for holding the scanning head 550 when not in use.

Figure 10A:
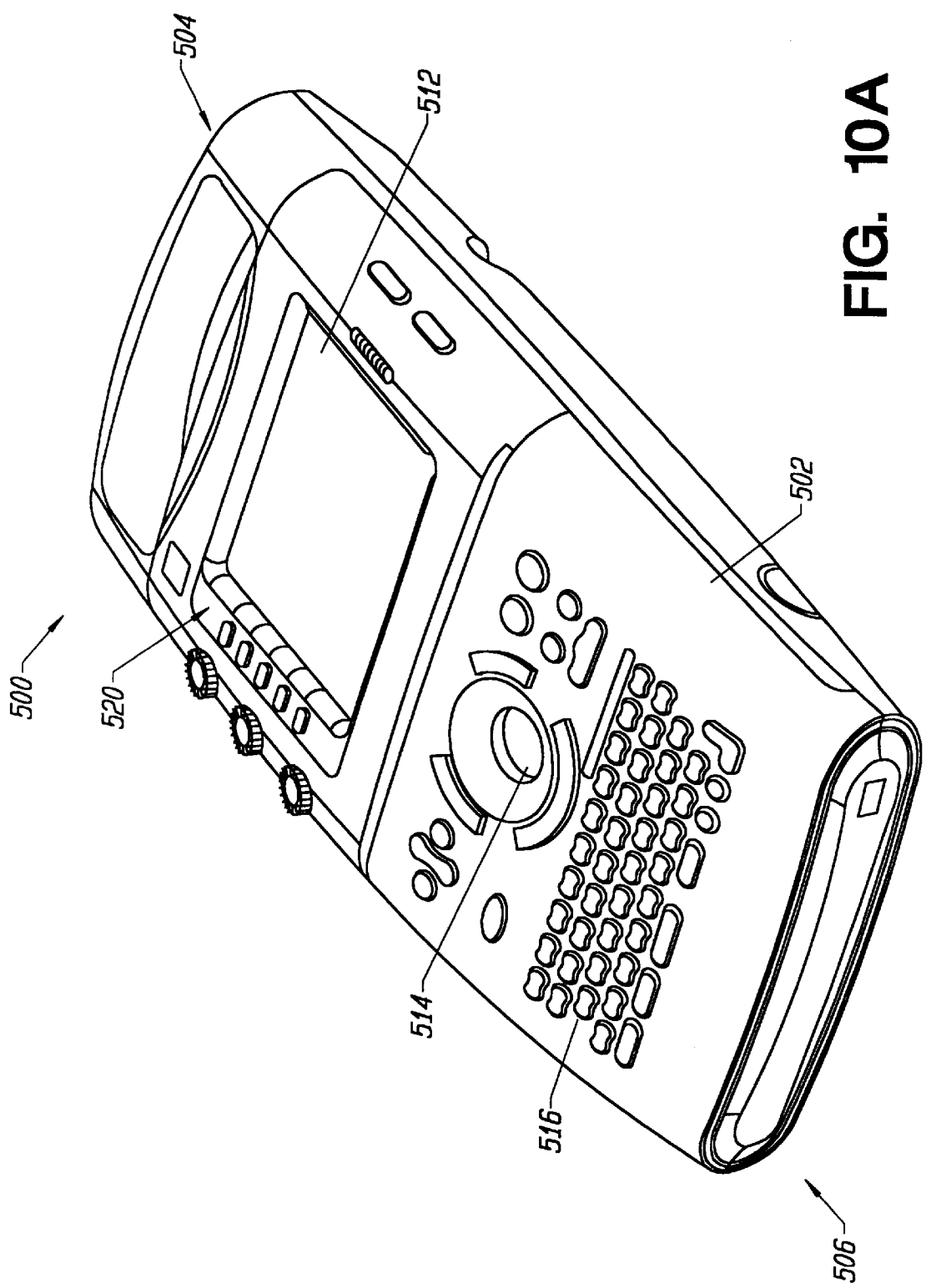
FIGS. 10A–10H are front perspective, back perspective, front, back, right side, left side, top, and bottom views, respectively, of a presently preferred embodiment of the hand held ultrasonic device of the present invention.
Figure 10B:
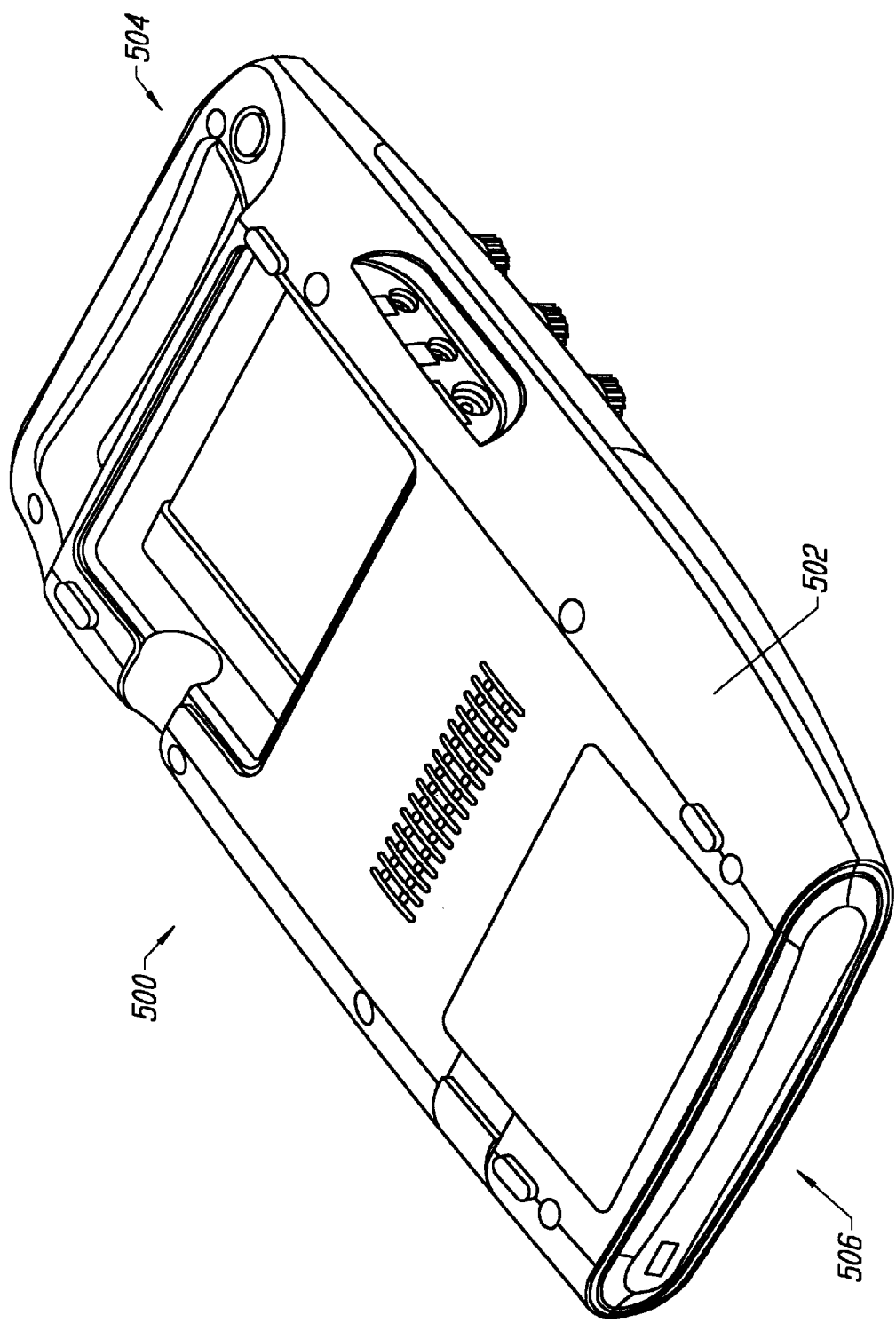
Figure 10C:
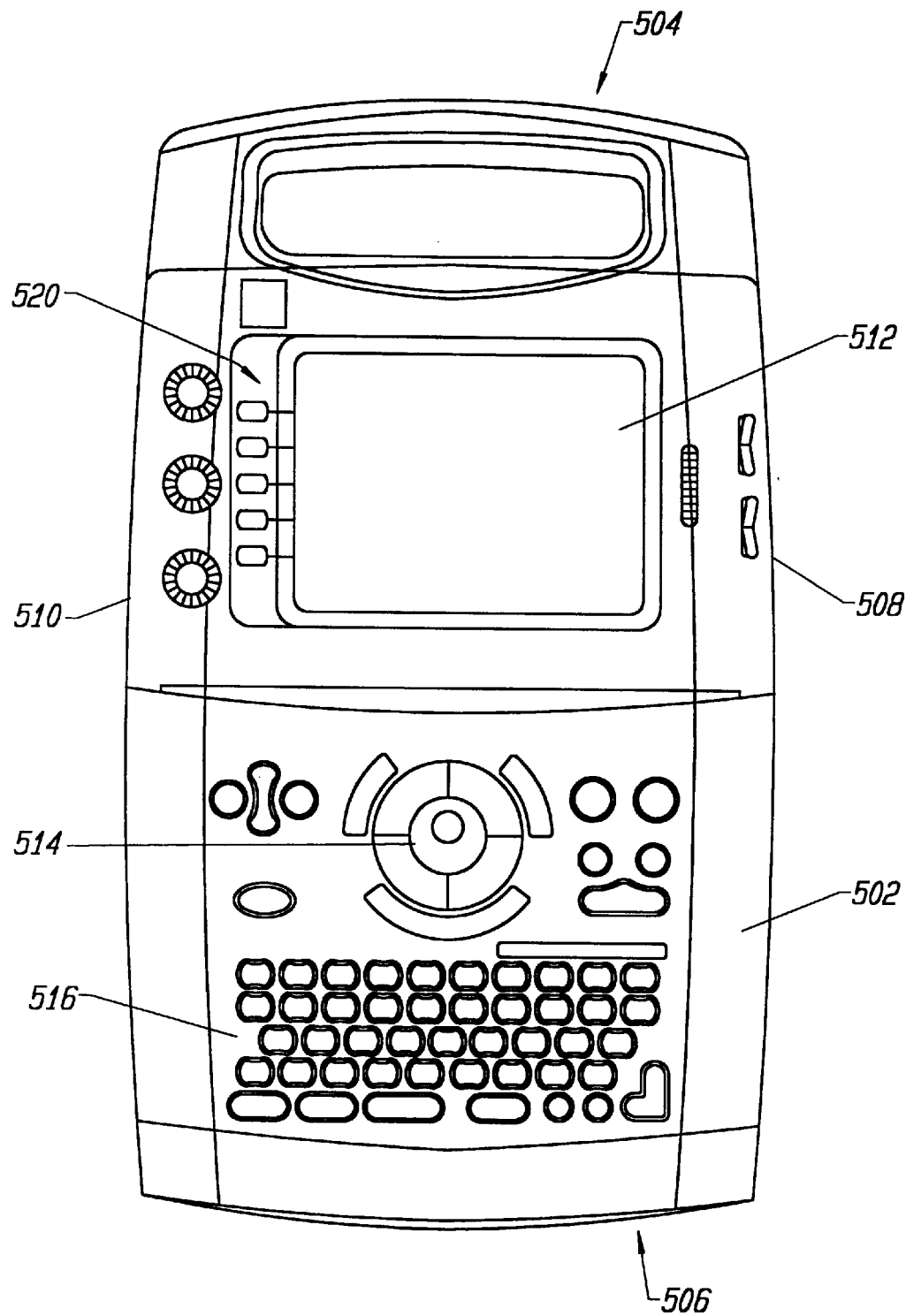
Figure 10D:
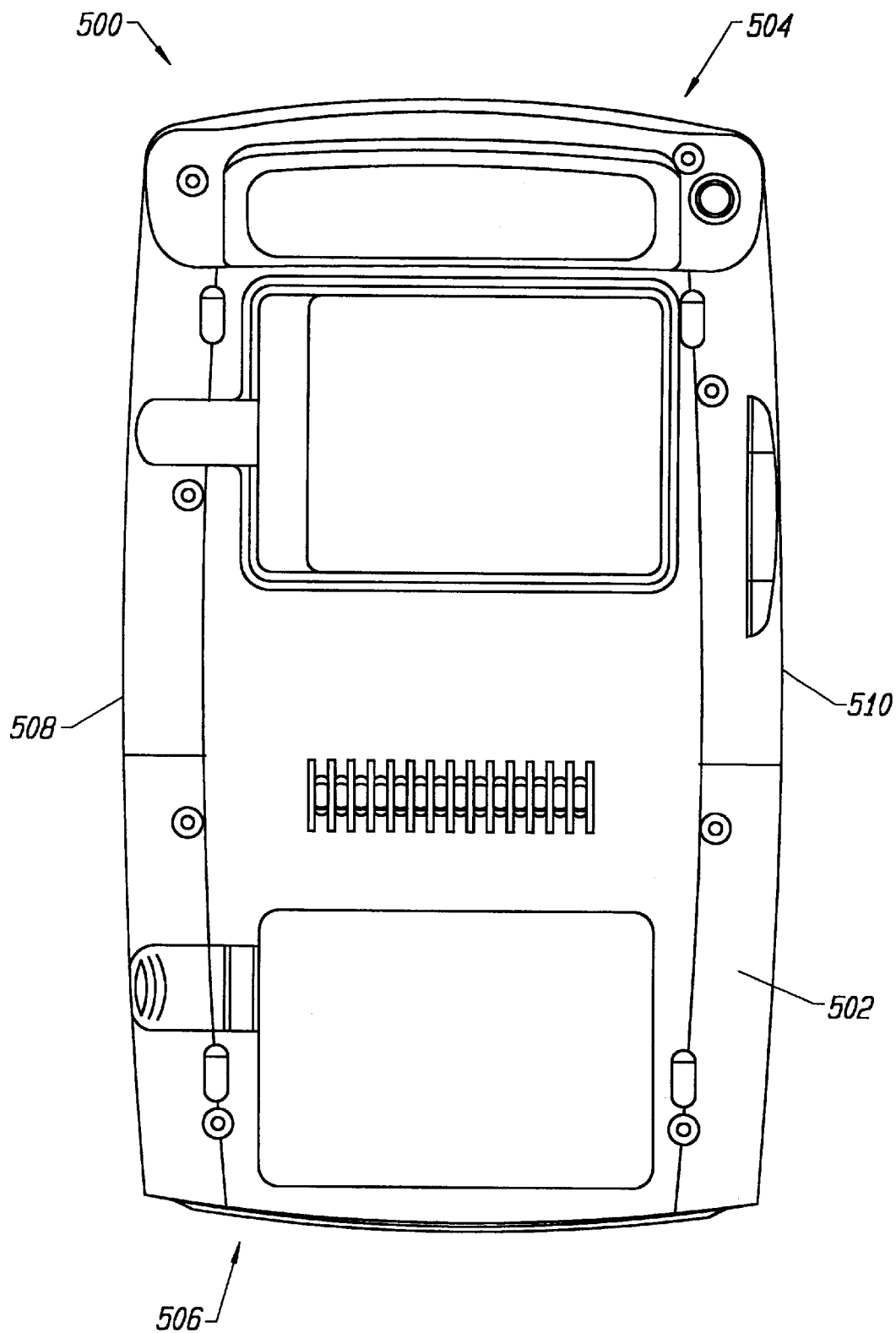
Figure 10E:
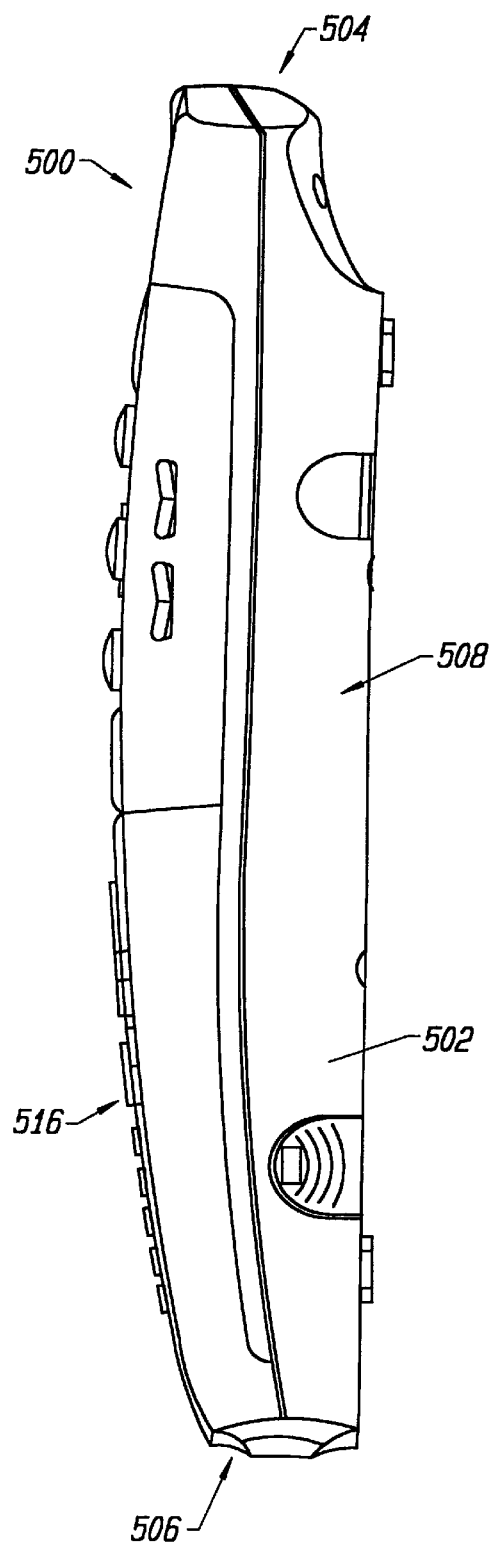
Figure 10F:
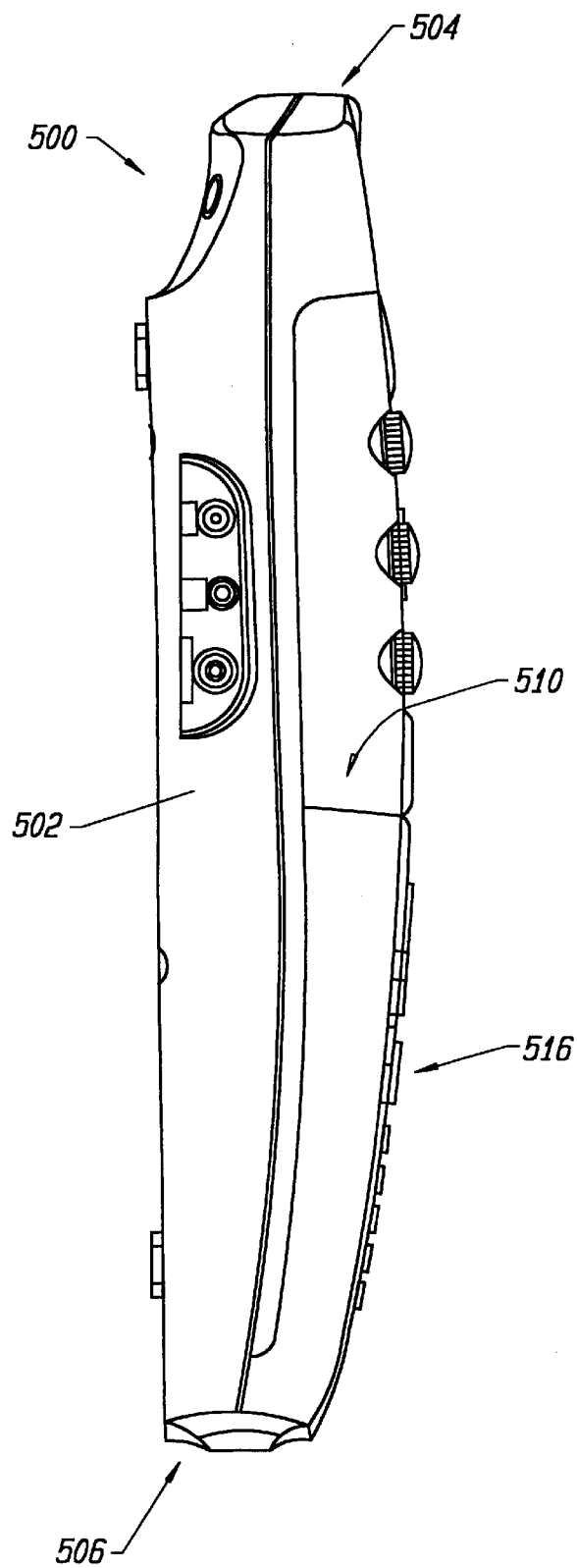
Figure 10G:
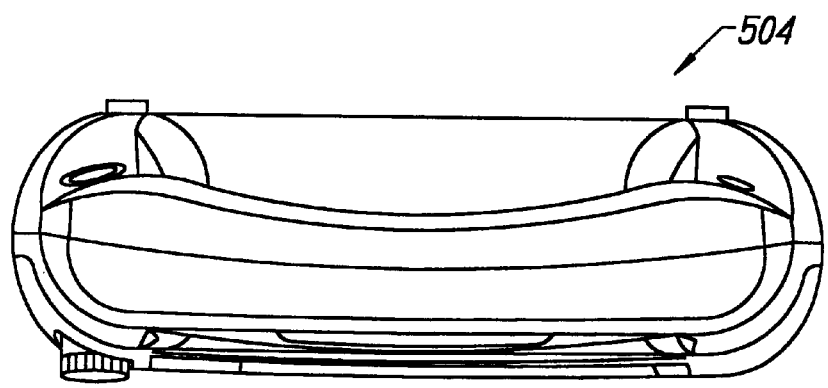
Figure 10H:
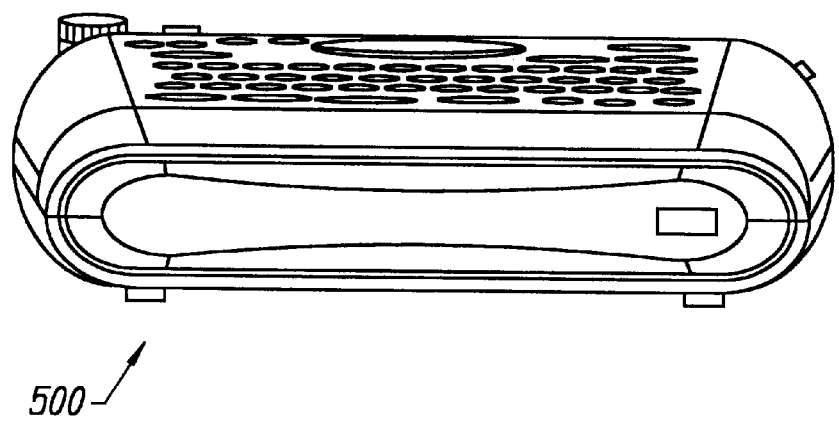
Figure 11A:
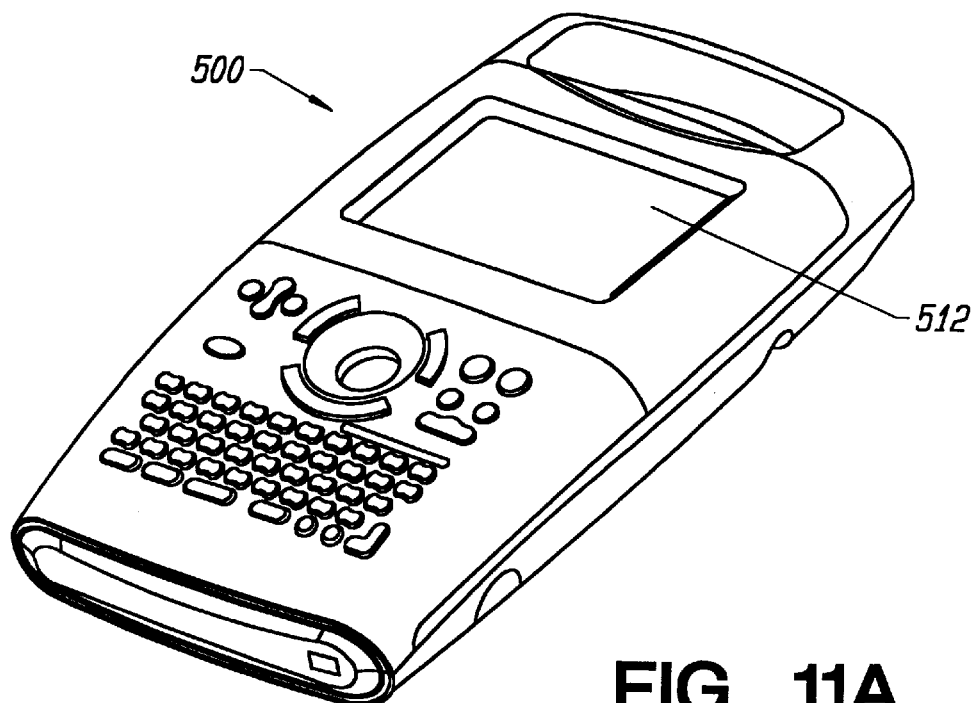
FIGS. 11A and 11B illustrate the adjustable display unit of the device of FIGS. 10A–10F.
Figure 11B:
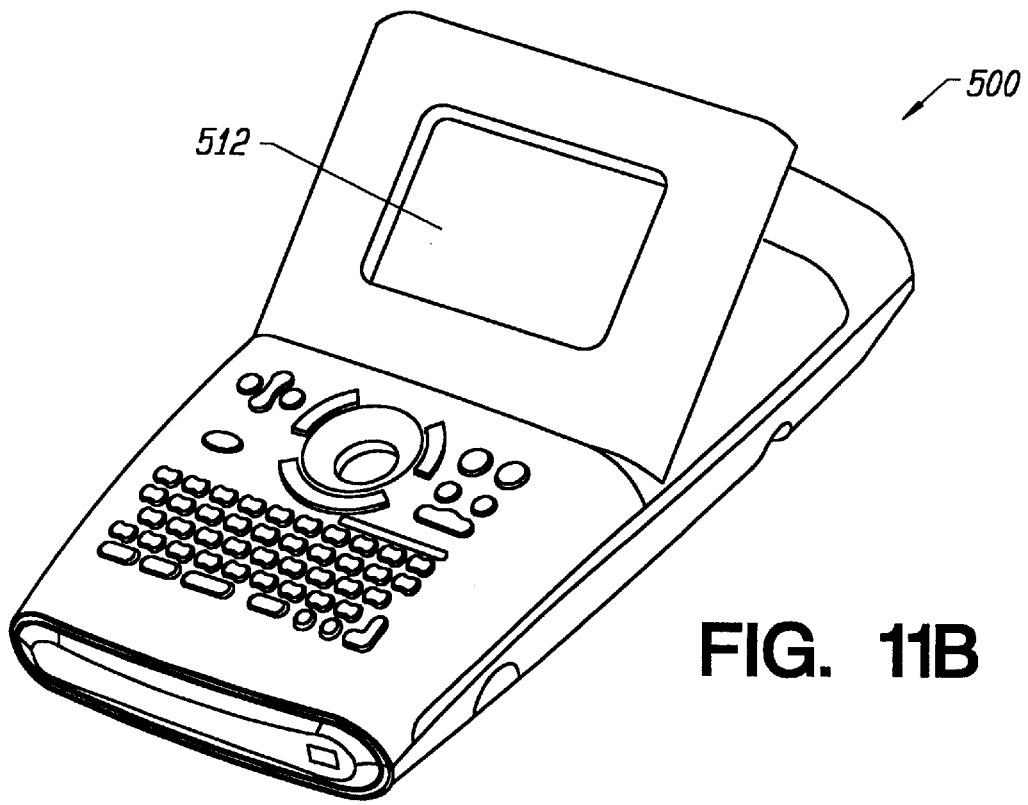
Figure 12A:
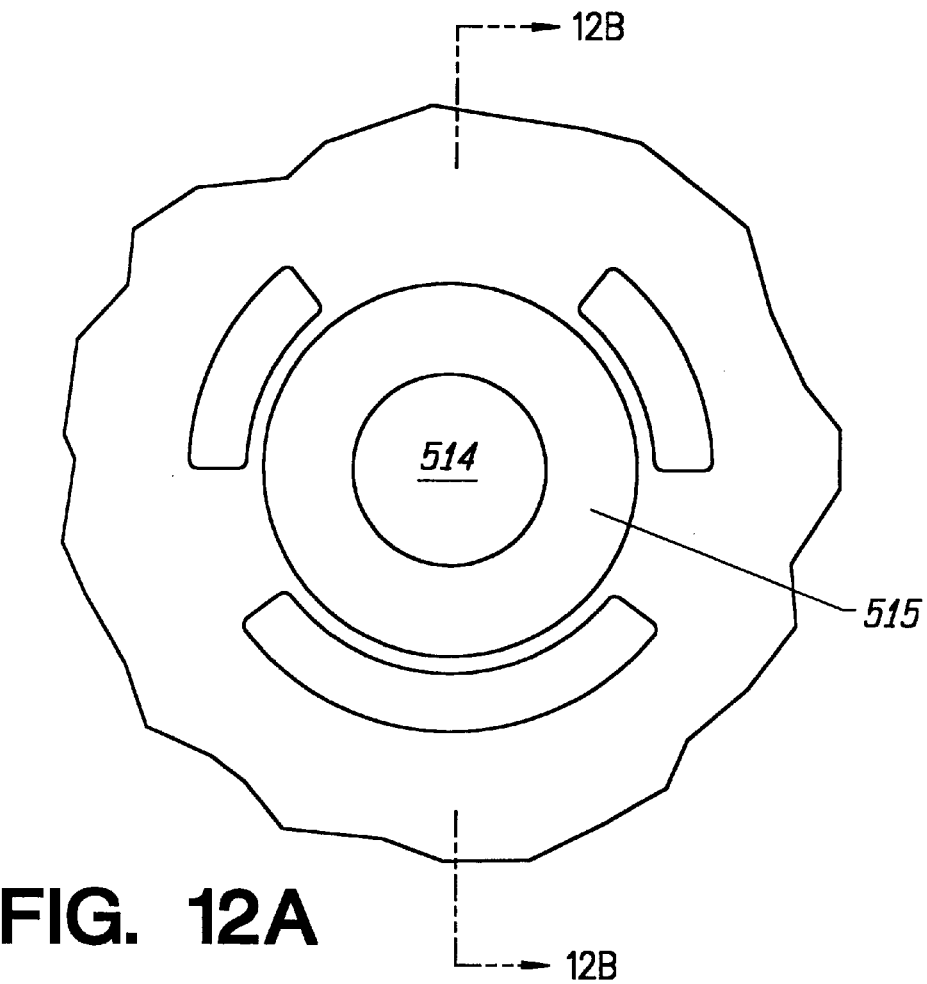
FIGS. 12A and 12B illustrate the recessed trackball of the device of FIGS. 10A–10F.
Figure 12B:
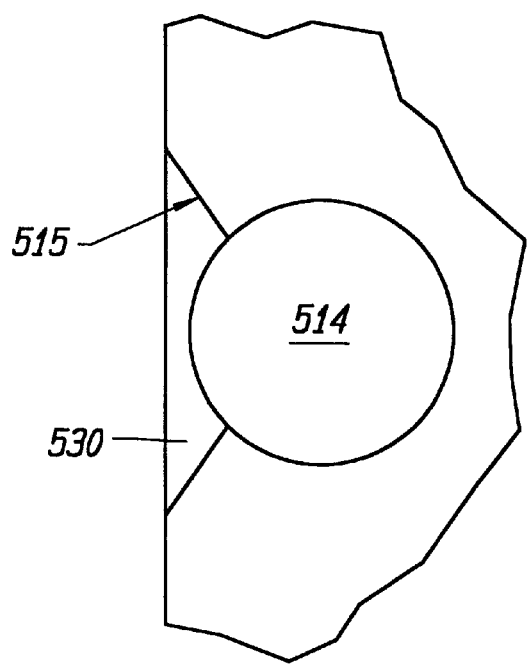

Referring now to FIGS. 10A–10H, a presently preferred design for the hand held ultrasonic imaging device 500 will be described. The device 500 comprises an enclosure 502 which is preferably formed from a hard plastic by conventional fabrication processes. The enclosure has a top end 504 (FIG. 10G), a bottom end 506 (FIG. 10H), a front face (FIG. 10C), a back face (FIG. 10D), a right side 508 (FIG. 10E), and a left side 510 (FIG. 10F). A display 512 and a multiplicity of user controls are provided on the front face, as shown in FIGS. 10A and 10C. The display 512 can be adjusted by inclining or pivoting a display support relative to the enclosure 502, as best illustrated in FIGS. 11A and 11B. The controls include both dedicated (single-function) buttons as well as multiple function buttons. Additionally, a roller ball 514 as well as an alphanumeric keyboard 516 are provided to permit data entry (patent name, characterising, etc.) as well as function selection. The roller ball 514 is preferably recessed in a well 515 formed in the enclosure 502, as best illustrated in FIGS. 12A and 12B, in order to avoid damage if the unit is accidentally dropped or hit against a surface.

In addition, five menu buttons 520 are provided in a linear arrangement next to the display screen 512 to permit linking of the buttons to corresponding software menu options displayed on the screen. The options, of course, may change from time to time. The dedicated push buttons include those intended for image freezing, image zooming, saving the image, power, patient information entry, patient examination information entry, and the like. It will be appreciated by providing both dedicated function buttons as well multiple function buttons and keyboard data entry, maximum flexibility in use of the hand held device can be achieved.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A hand held ultrasound device comprising:
   an enclosure having a front, a top, and a bottom;
   a display disposed in an upper section of the front of the enclosure;
   an acoustic window in the bottom of the enclosure; and
   an ultrasonic transducer and transceiver circuitry within the enclosure; and
   controls on the front of the enclosure below the display and above the acoustic window to permit a user to control an image acquired by the transducer through the acoustic window on the display.

2. A hand held ultrasonic device as in claim 1, further comprising a handle formed in or on the top of the enclosure.

3. A hand held ultrasonic device as in claim 2, further comprising a battery within the enclosure and electrical connectors on or near the bottom of the enclosure, wherein the electrical connectors are configured to permit removable connection to a battery recharger.

4. A hand held ultrasonic device as in claim 1, wherein the display is an LCD display.

5. A hand held ultrasonic device as in claim 1, wherein the display is inclined relative to a plane of the front of the enclosure.

6. A hand held ultrasonic device as in claim 1, wherein the display is flat relative to the plane of the enclosure.

7. A hand held ultrasonic device as in claim 1, wherein the display is pivotally mounted on the enclosure to permit user adjustment of the viewing angle.

8. A hand held ultrasonic device as in claim 1, wherein the ultrasonic transducer is an array transducer and the device further comprises a beamformer mounted in said enclosure and coupled to said transceiver circuit, for controlling the transmission of the ultrasonic waves by said array transducer and delaying and combining echo signals received by said elements of said array transducer to form an ultrasonic beam.

9. A hand held ultrasonic device as in claim 8, wherein said transceiver circuit includes transducer element drivers responsive to said beamformer for selectively exciting said transducer elements, and a multiplexer circuit, coupled to said transducer element drivers, said transducer elements, and said beamformer for alternately causing said transducer elements to be excited by said drivers and to receive echo signals for said beamformer.

10. A hand held ultrasonic device as in claim 1, wherein the controls comprise an on and off switch.

11. A hand held ultrasonic device as in claim 1, wherein the controls comprise an operating mode selector which permits selection between at least B mode and Doppler.

12. A hand held ultrasonic device as in claim 1, wherein the controls include a cursor control which permits a user to select from options presented on the display.

13. A hand held ultrasonic device as in claim 12, wherein the cursor control comprise s a roller ball recessed in the front of the enclosure.

14. A hand held ultrasonic device as in claim 1, wherein the controls include a dedicated freeze frame control.

15. A hand hold ultrasonic device as in claim 1, wherein the controls include a dedicated replay control.

16. A hand held ultrasonic device as in claim 1, wherein the controls include a full function alphanumeric keyboard.

17. A hand held ultrasonic device as in claim 1, further comprising additional controls to a side of the display on the enclosure.

18. A hand held ultrasonic device as in claim 17, wherein the additional controls are menu buttons arranged in a linear array adjacent to the side of the display.

19. A system comprising:
   A hand held ultrasonic device as in claim 1; and
   a recharger configured to removably connect to the electrical connectors on the enclosure of the hand held ultrasonic device.

20. A system as in claim 19, wherein the electrical connectors are disposed near the bottom of the enclosure and wherein the recharger includes a receptacle for removably receiving and holding the hand held ultrasonic device and electrical connectors within the receptacle which mate with the electrical connectors on the device enclosure to permit recharging when the device is in the receptacle.

21. A system as in claim 20, wherein the acoustic window is positioned on the enclosure so that it lies within the receptacle when the device is in the recharger.

* * * * *